US011319279B2

(12) United States Patent
Kim et al.

(10) Patent No.: US 11,319,279 B2
(45) Date of Patent: May 3, 2022

(54) ANTIMICROBIAL COMPOUND AND USE THEREOF

(71) Applicant: Korea Research Institute of Bioscience and Biotechnology, Daejeon (KR)

(72) Inventors: Won Gon Kim, Daejeon (KR); Hyun Ju Kim, Daejeon (KR); Yu Jin Kim, Daejeon (KR); Kyung Yun Cho, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 17/092,949

(22) Filed: Nov. 9, 2020

(65) Prior Publication Data

US 2021/0053909 A1 Feb. 25, 2021

Related U.S. Application Data

(63) Continuation of application No. 15/311,245, filed as application No. PCT/KR2015/004824 on May 14, 2015, now abandoned.

(30) Foreign Application Priority Data

May 15, 2014 (KR) .................. 10-2014-0058522

(51) Int. Cl.
| | |
|---|---|
| *C07C 235/64* | (2006.01) |
| *C07C 233/75* | (2006.01) |
| *C07C 235/56* | (2006.01) |
| *C07C 237/42* | (2006.01) |
| *A61K 31/166* | (2006.01) |
| *A61K 31/135* | (2006.01) |
| *A61K 45/06* | (2006.01) |
| *A61K 35/66* | (2015.01) |

(52) U.S. Cl.
CPC .......... *C07C 233/75* (2013.01); *A61K 31/135* (2013.01); *A61K 31/166* (2013.01); *A61K 45/06* (2013.01); *C07C 235/56* (2013.01); *C07C 235/64* (2013.01); *C07C 237/42* (2013.01); *A61K 35/66* (2013.01); *Y02A 50/30* (2018.01)

(58) Field of Classification Search
None
See application file for complete search history.

(56) References Cited

U.S. PATENT DOCUMENTS

2011/0117592 A1 5/2011 Wall

FOREIGN PATENT DOCUMENTS

| KR | 10-2013-0011204 A | 1/2013 |
| KR | 10-2014-0048745 A | 4/2014 |
| WO | 2015-003816 A2 | 1/2015 |

OTHER PUBLICATIONS

Alexander Schmitz et al., "Corallorazines from the *Myxobacterium corallococcus* coralloides", Journal of Natural Products, Jan. 14, 2014, pp. 159-163, vol. 77.
Sascha Baumann et al., "Cystobactamids: Myxobacterial Topoisomerase Inhibitors Exhibiting Potent Antibacterial Activity", Angewandte Chemie International Edition, 2014, pp. 14605-14609, vol. 53, Wiley-VCR Verlag GmbH & Co., KGaA, Weinheim.
Sooyeon Park et al., "Isolation and Characterization of Bacteriolytic Wild Myxobacteria", Korean Journal of Microbiology and Biotechnology, 2004, pp. 218-223, vol. 32, No. 3, Republic of Korea, with English Abstract.
International Search Report in connection with PCT International Application No. PCT/KR2015/004824 dated Aug. 3, 2015.
Korean Office Action in connection with Korean application No. 10-2015-0067158 dated Dec. 7, 2016, with English Machine Translation.
Korean Notice of Allowance in connection with Korean application No. 10-2015-0067158 dated Jun. 7, 2017, with English Machine Translation.
Silva Sonjak et al., "Comparison of secondary metabolite production by Penicillium crustosum strains, isolate from Arctic and other various ecological niches", FEMS Microbiology Ecology, 2005, pp. 51-60, vol. 53.
Gupte et al., "Antifungal Antibiotics", Appl Microbiol Biotechnol, 2002, pp. 46-57, vol. 58.
The Apr. 2, 2014, Entry for the blog "Nature's Pulchritude".
Ed Murry et al., "Toxicological Profile for Propylene Glycol", U.S. Department of Health and Human Services, 1997.
A. J. Martinez-Murcia et al., "Patterns of sequence variation in two regions of the 16s rRNA multigene family of *Escherichia coli*" Int. J System. Bacterial., 1999, pp. 601-610, vol. 49.
Ines Gharbi et al., "Butylated hydroxytoluene (BHT) emitted by fungi naturally occurring in olives during their pre-processing storage for improving olive oil stability", Eur J. Lipid Sci. Technol., 2017, vol. 119, Paper 1600343.
Yao Xiao et al., "Antibiotic Production by Myxobacteria Plays a Role in Predation", J. Bacterial., Sep. 2011, pp. 4626-4633, vol. 193, No. 18.

*Primary Examiner* — Fred H Reynolds
(74) *Attorney, Agent, or Firm* — Hauptman Ham, LLP

(57) ABSTRACT

The present invention relates to: coralmycin A and B, which are novel compounds exhibiting antimicrobial activity, an isomer thereof, a derivative thereof or a pharmaceutically acceptable salt thereof; a microorganism of the genus *Corallococcus* producing the same; and an antimicrobial use thereof.
The coralmycin A and B have very strong antimicrobial activity against antibiotic-resistant bacteria such as MRSA, QRSA, VRE, VISA, etc.; *Acinetobacter baumannii*, which is a multidrug-resistant microorganism; and also against gram-positive microorganisms and gram-negative microorganisms. Therefore, the present invention can be very useful for prevention, treatment and alleviation of various microbial infections, and thus can be widely applied to the medical supply, quasi-drug, food, and feed industries.

19 Claims, 1 Drawing Sheet

Specification includes a Sequence Listing.

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: 27F primer

<400> SEQUENCE: 1
gagtttgatc ctggctcag                                                19

<210> SEQ ID NO 2
<211> LENGTH: 20
<212> TYPE: DNA
<213> ORGANISM: Artificial Sequence
<220> FEATURE:
<223> OTHER INFORMATION: 1544R primer

<400> SEQUENCE: 2
agaaaggagg tgatccagcc                                               20

ANTIMICROBIAL COMPOUND AND USE THEREOF

CROSS-REFERENCE TO RELATED APPLICATION

This application is a continuation of U.S. patent application Ser. No. 15/311,245, filed on Feb. 28, 2017, which is the National Phase application of International Application No. PCT/KR2015/004824 filed May 14, 2015, which is based upon and claims the benefit of priorities to Korean Patent Application No. 10-2014-0058522 filed on May 15, 2014, in the Korean Intellectual Property Office, which are incorporated herein in their entireties by reference.

REFERENCE TO A SEQUENCE LISTING

This application incorporates-by-reference nucleotide and/or amino acid sequences which are contained in the text file (Sequence Listing) filed as part of this application.

TECHNICAL FIELD

The present invention relates to an antimicrobial compound and a microorganism having an antimicrobial activity, and more specifically, to a novel compound having an antimicrobial activity, an isomer thereof, a derivative, or pharmaceutically acceptable salt thereof; a microorganism of the genus *Corallococcus* producing the same; an antimicrobial composition containing the same; a pharmaceutical composition for preventing or treating microbial infections containing the composition; an antimicrobial quasi-drug composition; an antimicrobial food composition; an antimicrobial feed composition for livestock or fish; and a method for preparing the compound.

BACKGROUND ART

With the frequent use of antibiotics, the incidence of resistance to antibiotics has also increased. As such, to cope with essential life-threatening problems, it has been a major issue to discover and develop a novel antibiotic material. Since the first global report of the vancomycin-resistant *Staphylococcus aureus* (VRSA), which shows a high level of resistance to vancomycin that had been referred to as the last therapeutic agent for *Staphylococcus aureus* (the most frequent pathogen of human infections), by the US Centers for Disease Control (CDC) in 2002, there is a growing risk of diffusion of so-called superbacteria. In fact, since methicillin-resistant *S. aureus* (MRSA), which is treatable by only a few antibiotic including vancomycin, had been an issue in the 1970s, vancomycin-resistant *Enterococcus* (VRE) was first discovered in Europe in 1988. Then, the appearance of vancomycin intermediate-resistant *S. aureus* (VISA) was reported in Japan, the United States, France, and Korea in the late 1990s. These new examples, raised as a global crisis of antibiotic resistance, have shown the seriousness of the resistance, and thus there is an urgent need for the development of antibiotics with a new concept. In particular, no specific treatments have been developed for multidrug-resistant gram-negative bacteria and thus there is an urgent need for the development of novel anti-gram-negative antibiotics.

For the development of novel antibiotic materials, rather than producing derivatives of the existing antibiotics via modification, as a preferred approach for overcoming resistant bacteria, it is more appropriate to develop antibiotics by discovering totally new targets (KR Patent Application Publication No. 10-2014-0048745).

DISCLOSURE

Technical Problem

Under the circumstances, the present inventors have made efforts to discover a novel antibiotic material, and as a result, they have newly identified a Myxobacteria microorganism producing a strong antibiotic material, isolated and purified the antibiotic material with purity from the culture broth of the microorganism, determined the chemical structure of the antibiotic material, and confirmed that the antibiotic material has an antimicrobial activity not only in gram-positive and gram-negative microorganisms but also in antibiotic-resistant microorganisms, thereby completing the present invention.

Technical Solution

An object of the present invention is to provide a compound represented by the following Formula 1 or 2, an isomer thereof, a derivative, or a pharmaceutically acceptable salt thereof.

[Formula 1]

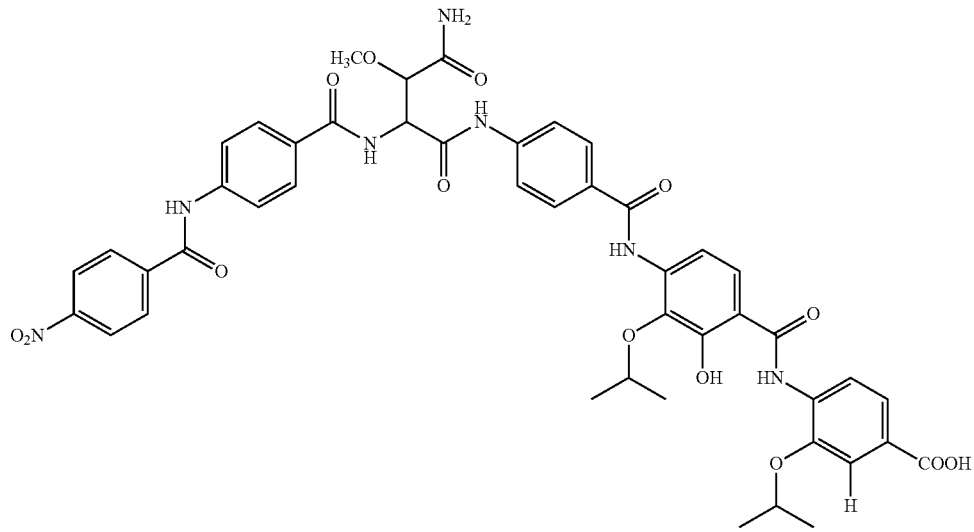

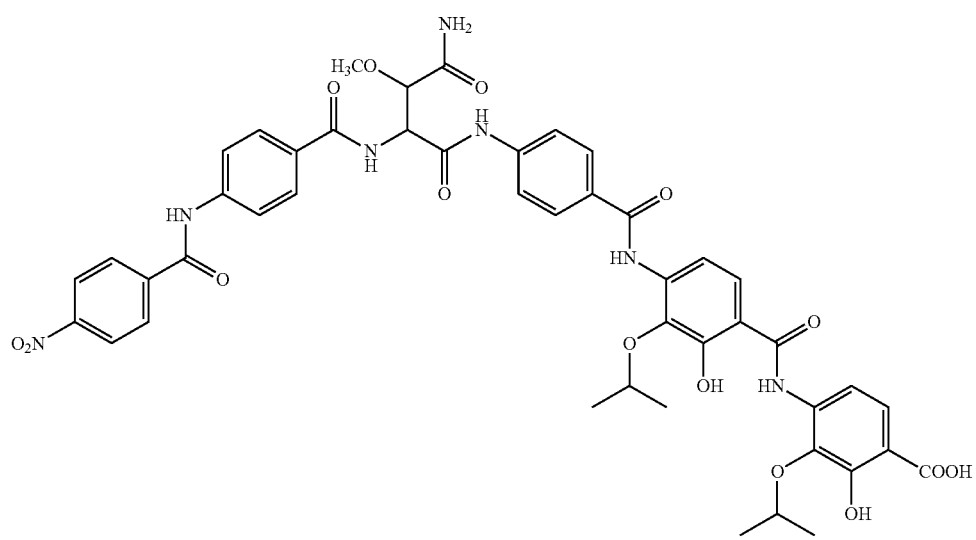

[Formula 2]

Another object of the present invention is to provide a microorganism of the genus *Corallococcus* having an antimicrobial activity, wherein the microorganism produces the compound represented by Formula 1 or 2 above, an isomer thereof, a derivative thereof, or a pharmaceutically acceptable salt thereof.

Still another object of the present invention is to provide an antimicrobial composition containing the compound represented by Formula 1 or 2 above, an isomer thereof, a derivative thereof, or a pharmaceutically acceptable salt thereof, a microorganism of the genus *Corallococcus* producing the same, a spore of the microorganism, a culture broth of the microorganism, an extract of the microorganism, a fraction of the extract, or a mixture thereof.

Still another object of the present invention is to provide a method for treating at least one disease selected from the group consisting of (i) to (iii) below, including administering the composition to a subject in need thereof:

(i) pyogenic infection;

(ii) food poisoning; and (iii) bacteremia, sepsis, urinary tract infection, pneumonia, pleural empyema, tympanitis, mastoiditis, meningitis, osteomyelitis, arthritis, peritonitis, pericarditis, cellulitis, typhus, and acute gastroenteritis.

Still another object of the present invention is to provide a method for preparing compounds represented by Formula 1 or 2 above, an isomer thereof, a derivative thereof, or a pharmaceutically acceptable salt thereof.

Still another object of the present invention is to provide a use of the above compounds, an isomer thereof, a derivative, or a pharmaceutically acceptable salt thereof, a microorganism of the genus *Corallococcus* producing the same, a spore of the microorganism, a culture broth of the microorganism, an extract of the microorganism, a fraction of the extract, or a mixture thereof for the preparation of pharmaceutical drugs for treating at least one disease selected from the group consisting of (i) to (iii) above.

Advantageous Effects of the Invention

The microorganism of the genus *Corallococcus* producing coralmycins A and B, which are novel compounds of the present invention, have very strong antimicrobial activities against not only the gram-positive and gram-negative microorganisms but also antibiotic-resistant microorganisms, such as MRSA, QRSA, VRE, and VISA, and *Acinetobacter baumannii*, which is a multidrug-resistant microorganism. Therefore, the present invention can be very useful for prevention, treatment, and alleviation of various microbial infections, and thus can be widely applied to the medical supply, quasi-drug, food, and feed industries.

BEST MODE

Figure 1A:
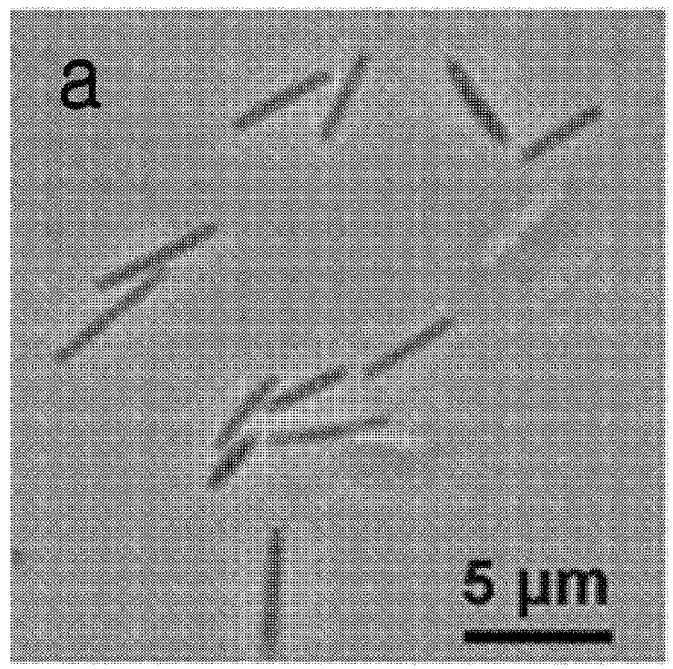
FIG. 1A shows an image of cells of a *Corallococcus coralloides* M23 microorganism.

To achieve the above objects, in an aspect, the present invention provides a compound represented by the following Formula 1 or 2, an isomer thereof, a derivative thereof, or a pharmaceutically acceptable salt thereof.

[Formula 1]

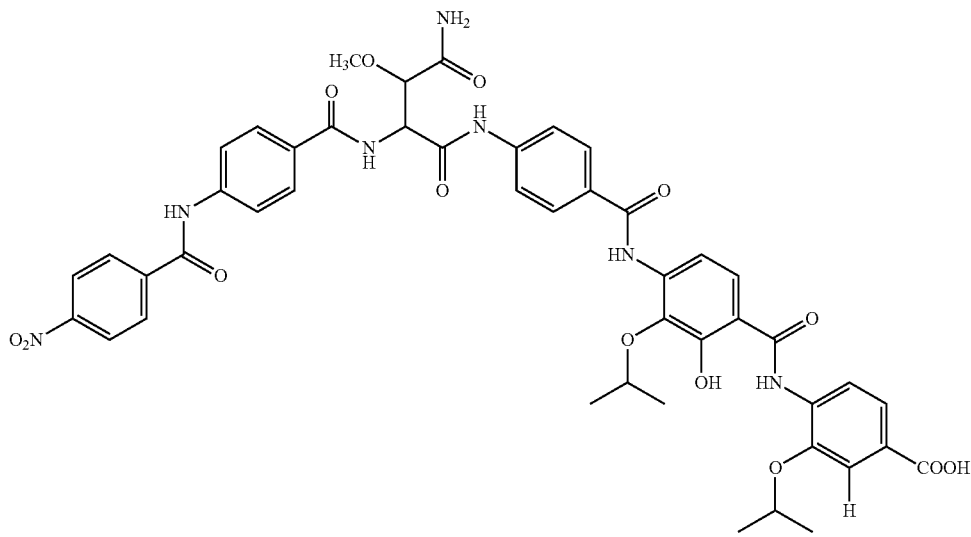

[Formula 2]

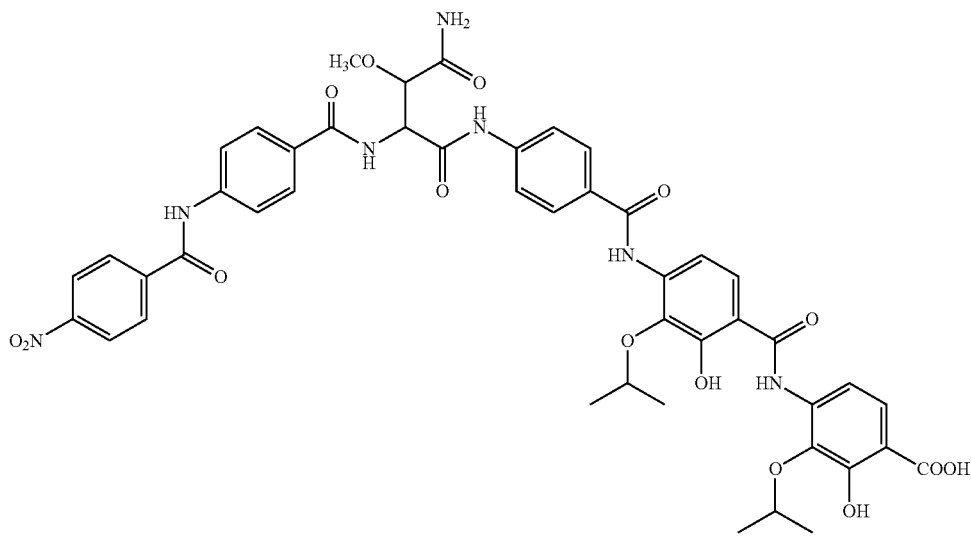

In the present invention, the *Corallococcus coralloides* M23 microorganism (Accession No. KCTC18279P), which is a microorganism of the genus *Corallococcus*, was identified, and two different compounds with antimicrobial activities produced by the microorganism were purified and identified. As a result, it was first confirmed that one of the compounds is a novel compound represented by Formula 1 above (hereinafter, "coralmycin A") and the other compound is a novel compound represented by Formula 2 above (hereinafter, "coralmycin B").

Additionally, the microorganism (Accession No. KCTC18279P) was deposited to the Korean Collection for Type Cultures (KCTC), which is an international depositary authority under the Budapest Treaty, and assigned the Accession No. KCTC12812BP. Accordingly, in the present invention, KCTC18279P and KCTC12812BP can be interchangeably used as the Accession No. of the *Corallococcus coralloides* M23 microorganism.

Specifically, the compounds of the present invention may include isomers, a derivative thereof, or a pharmaceutically acceptable salt thereof having the same activities as those of the compounds represented by Formula 1 or 2 above, but are not limited thereto.

As used herein, the term "isomers" refers to a relationship of molecules which have the same chemical formula but are not the same. Examples of the types of isomers include structural isomers, geometrical isomers, optical isomers, and stereoisomers. Structural isomers are compounds which have the same chemical constitution but differ in the three-dimensional orientations of their atoms and groups in space; in which optical isomers (i.e., enantiomers) refer to two stereoisomers of a compound which have mirror images that are not superimposable with each other, and diastereomers refer to two or more stereoisomers of a compound which have an achiral center but whose molecules are not mirror images of each other.

For example, the isomers of Formula 1 or 2 above may be those represented by Formula 3 or 4 below, but are not limited thereto.

[Formula 3]

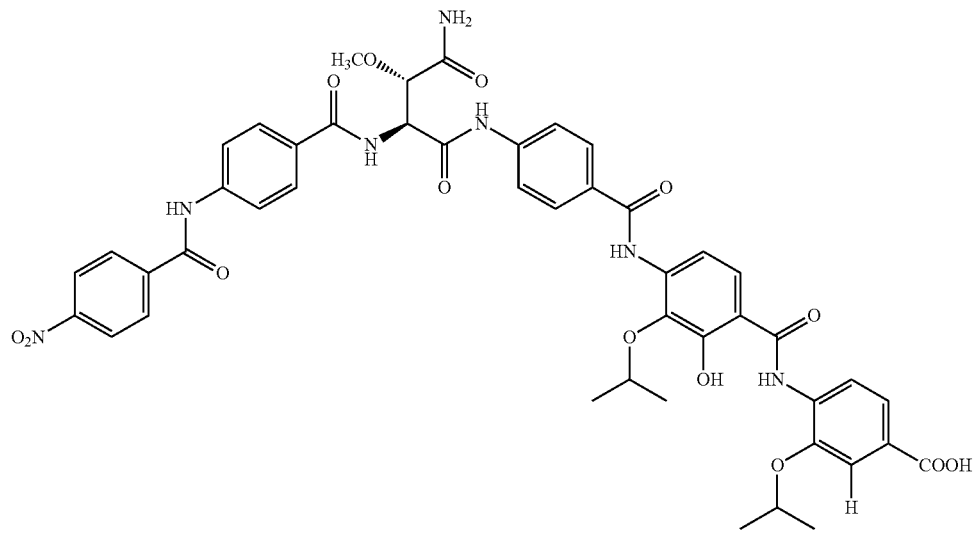

[Formula 4]

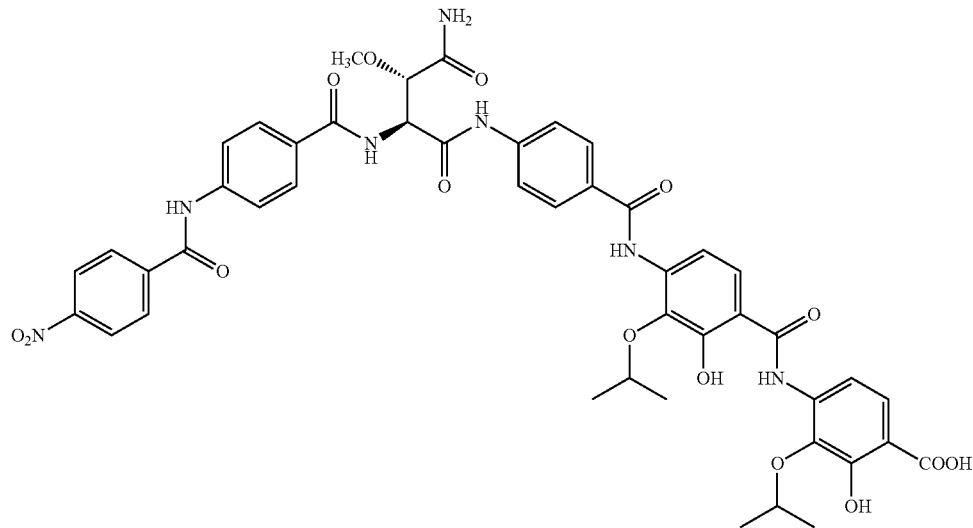

As used herein, the term "derivative" refers to a compound in which an atom or atomic group of a compound is substituted with a different atom or atomic group. In the present invention, the derivatives of coralmycin A or coralmycin B are compounds having an antimicrobial activity in which the atom or atomic group of coralmycin A or coralmycin B are substituted with a different atom or atomic group. Specifically, the derivatives may be those in which the hydrogen atom in a hydrocarbon or heterocycle is substituted with a different group or a functional group is substituted with a different functional group.

As used herein, the term "pharmaceutically acceptable salt" refers to any of all organic or inorganic addition salts of the compound, which do not diminish the advantageous effects of the compounds represented by Formula 1 or 2 above, in a concentration which is relatively non-toxic to patients, and has an unharmful and effective action.

Acid addition salts may be prepared by a conventional method, for example, dissolving a compound in an excess amount of an aqueous acid solution and precipitating the resulting salt in a water-miscible organic solvent (e.g., methanol, ethanol, acetone, or acetonitrile). An equimolar amount of a compound and an acid or alcohol in water (e.g., glycol monomethylether) may be heated and then the mixture may be dried by evaporation or the precipitate may be subjected to suction filtration, but is not limited thereto.

In particular, organic acids and inorganic acids may be used as a free acid. Examples of the inorganic acids may include hydrochloric acid, phosphoric acid, sulfuric acid, nitric acid, and tartaric acid; organic carbonic acids such as methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc., but are not limited thereto.

Additionally, a pharmaceutically acceptable metal salt may be prepared using a base. An alkali metal salt or alkali earth metal salt may be prepared, for example, by dissolving a compound in an excess amount of an alkali metal hydroxide or alkali earth metal hydroxide solution, filtering a non-dissolved compound salt obtained therefrom, and evaporating the filtrate, followed by drying. In particular, examples of a pharmaceutically acceptable metal salt to be prepared may include sodium, potassium, or calcium salts, but are not limited thereto. Additionally, a corresponding silver salt may be prepared by reacting an alkali metal or alkali earth metal salt with an appropriate silver salt (e.g., silver nitrate), but the preparation method is not limited thereto.

The pharmaceutically acceptable salts of the compounds represented by Formula 1 or 2 above may include salts of an acidic or basic group that can be present in the compounds of Formula 1 or Formula 2, unless instructed otherwise. For example, the pharmaceutically acceptable salts may include sodium, calcium, or potassium salts of a hydroxyl group, etc., and other pharmaceutically acceptable salts of an amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc., and they can be prepared by a preparation method known in the art.

As a pharmaceutically acceptable salt of the compounds of Formula 1 or 2 above, any pharmaceutically acceptable salt which exhibits the same antimicrobial activity as the compounds of Formula 1 or 2 above can be used without limitation.

In another aspect, the present invention provides a microorganism of the genus *Corallococcus* having an antimicrobial activity, where the microorganism can produce the compounds represented by Formula 1 or 2 above, an isomer thereof, a derivative thereof, or a pharmaceutically acceptable salt thereof.

In the present invention, the microorganism of the genus *Corallococcus* may belong to the scope of the present invention without limitation, as long as the microorganism can produce compounds represented by Formula 1 or 2 above, an isomer thereof, a derivative thereof, or a pharmaceutically acceptable salt thereof thereby having antimicrobial activities. Specifically, the microorganism may be *Corallococcus coralloides*, and more specifically, a *Corallococcus coralloides* M23 microorganism with the Accession Number of KCTC18279P, but is not limited thereto.

Figure 1B:
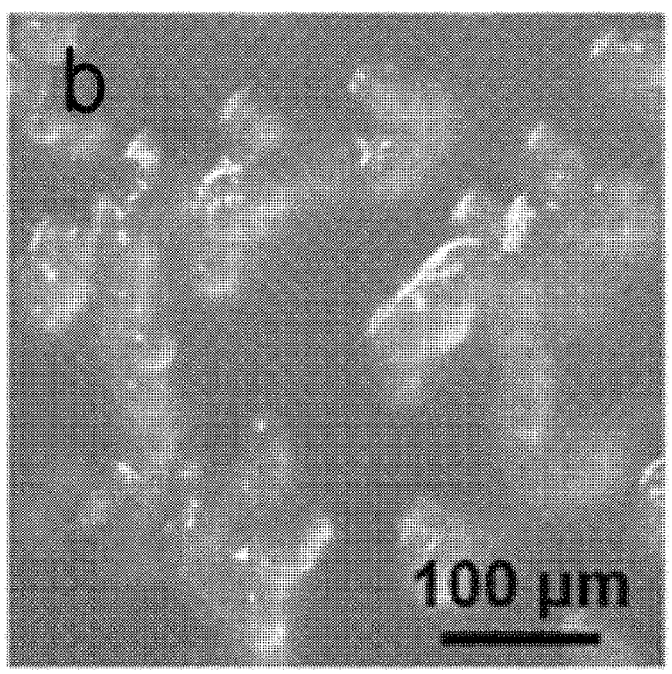
FIG. 1B shows an image of the shape of fruiting bodies of a *Corallococcus coralloides* M23 microorganism.

In an exemplary embodiment of the present invention, a physiological and morphological examination was performed for the identification of a *Corallococcus coralloides* M23 microorganism purely isolated from a soil sample. As a result, the microorganism was confirmed to be a gram-negative *Bacillus* with a length of about 4 μm (FIG. 1A), which showed vegetative growth feeding on *E. coli* and migrated with gliding motility. Additionally, the microorganism formed its unique fruiting bodies in WC medium (10 mM 3[N-morpholino]propanesulfonic acid (pH 7.6), 0.1% CaCl$_2$.2H$_2$O, 1.5% agar) (FIG. 1B).

Additionally, for the identification of the microorganism based on the nucleotide sequence of 16S rDNA, DNA was extracted from the microorganism and analyzed by PCR. As a result, it was confirmed that the nucleotide sequence of 16S rDNA of the M23 microorganism showed a similarity of 99.86% to that of 16S rDNA (Accession Number DQ768120) of the standard microorganism of *Corallococcus coralloides* (DSM 2259 (T)). Accordingly, the M23 microorganism was identified based on the physiological and morphological characteristics and the analysis of the nucleotide sequence of 16S rDNA, and the M23 microorganism was deposited to the Korean Collection for Type Culture (KCTC) located at 25 Gwahak-ro, Yuseong-gu, Daejeon, Korea, on Apr. 2, 2014, under Accession No. KCTC 18279P.

In still another aspect, the present invention provides a culture broth of the microorganism of the genus *Corallococcus*.

Specifically, the culture broth of the present invention may be a culture broth of a microorganism of the genus *Corallococcus*, and more specifically, a culture broth of the *Corallococcus coralloides* M23 microorganism with the Accession Number of KCTC18279P, but is not limited thereto. Since the compounds represented by Formula 1 or Formula 2 have an antimicrobial activity, the culture broth of the microorganism of the genus *Corallococcus* producing the above compounds will also have the antimicrobial activity.

As used herein, the term "culture broth" refers to the entire medium including a cultured microorganism obtained by culturing the microorganism of the genus *Corallococcus* of the present invention, specifically the *Corallococcus coralloides* M23 microorganism, in medium which can provide nutrients for growth and survival of the microorganism, for a particular period of time; a metabolite thereof; remaining nutrients, etc., and the culture solution in which the microorganism is removed after culturing is also included. Since the microorganism of the genus *Corallococcus* and the *Corallococcus coralloides* M23 microorganism are microorganisms having an antimicrobial activity, the microorganism of the genus *Corallococcus* or the *Corallococcus coralloides* M23 microorganism, and a culture broth thereof can be used as an antimicrobial composition.

In still another aspect, the present invention provides an antimicrobial composition containing the compound represented by Formula 1 or 2 above, an isomer thereof, a derivative thereof, or a pharmaceutically acceptable salt thereof, a microorganism of the genus *Corallococcus* producing the same, a spore of the microorganism, a culture broth of the microorganism, an extract of the microorganism, a fraction of the extract, or a mixture thereof. Specifically, the microorganism may be a *Corallococcus coralloides* microorganism, and more specifically, the *Corallococcus coralloides* M23 microorganism with the Accession Number of KCTC18279P, but is not limited thereto.

The compounds represented by Formula 1 or Formula 2 have very strong antimicrobial activities against antibiotic-resistant microorganisms, gram-positive microorganisms, and gram-negative microorganisms, and thus a composition containing a microorganism of the genus *Corallococcus* producing the same, a spore of the microorganism, a culture broth of the microorganism, an extract of the microorganism, a fraction of the extract, or a mixture thereof will also have a very strong antimicrobial activity.

As used herein, the term "extract" refers to a resulting product obtained by extracting a target material using water, a low-grade alcohol having 1 to 4 carbon atoms (e.g., methanol, ethanol, propanol, butanol, etc.), an organic solvent (e.g., hexane, acetone, chloroform, methyl acetate, etc.), a mixed solvent thereof, etc., and the resulting product includes all of an extract, a dilution or concentrate of the extract, a dried product obtained by drying the extract, or a crude purified or purified product, etc. For the purpose of the present invention, the extract is a resulting product obtained by extracting a microorganism of the genus *Corallococcus* using an organic solvent, and the extract may include an antimicrobial compound provided in the present invention, but is not limited thereto.

As used herein, the term "fraction" refers to a resulting product obtained by a fractionation method which separates particular components or particular groups from a mixture containing various constituting components. In the present invention, specifically, the fraction may be a resulting product obtained by subjecting the extract of microorganism of the genus *Corallococcus* to solvent fractionation using a solvent such as n-hexane, ethyl acetate, etc. The fraction may include both a polar solvent fraction and a non-polar solvent fraction, and specifically, a methanol fraction, an ethyl acetate fraction, etc., may be used as well.

As used herein, the terms "antimicrobial" or "antimicrobial activity" refer to properties that can resist against microorganisms such as bacteria and fungi, and more specifically, to the characteristics that antibiotic materials or the like being inhibiting the growth or proliferation of microorganisms.

For the purpose of the present invention, the terms antimicrobial and antimicrobial activity may be used as characteristics to inhibit the growth or proliferation of antibiotic-resistant or antibiotic-susceptible gram-positive microorganisms; antibiotic-resistant or antibiotic-susceptible gram-negative microorganisms; etc., but the uses of these terms are not particularly limited thereto.

The antibiotic-resistant microorganism may be a microorganism having a resistance to at least one antibiotic selected from the group consisting of penicillin antibiotics, methicillin antibiotics, quinolone antibiotics, vancomycin antibiotics, carbapenem antibiotics, and aminoglycoside antibiotics, and specifically, the microorganism may be methicillin-resistant *Staphylococcus aureus* (MRSA), quinolone-resistant *Staphylococcus aureus* (QRSA), vancomycin resistant *enterococcus* (VRE), vancomycin intermediate-resistant *S. aureus* (VISA), or multidrug-resistant *Acinetobacter baumannii*, but is not limited thereto.

In an exemplary embodiment of the present invention, the antimicrobial activities of coralmycin A against MRSA, QRSA, and multidrug-resistant *Acinetobacter baumannii* (i.e. antibiotic-resistant microorganisms) were confirmed, and the antimicrobial activities of coralmycin B against MRSA and multidrug-resistant *Acinetobacter* were confirmed (Tables 2 and 4).

The gram-positive microorganisms may be a microorganism of the genus *Staphylococcus*, the genus *Bacillus*, the genus *Streptococcus*, or the genus *Enterococcus*, and the gram-negative microorganisms may be a microorganism of the genus *Salmonella*, the genus *Acinebacter*, the genus *Escherichia*, the genus *Pseudomonas*, or the genus *Klebsiella*, but the microorganisms are not particularly limited thereto.

Specifically, the gram-positive microorganisms may be *Staphylococcus aureus*, MRSA, QRSA, *Bacillus subtilis*, *Bacillus cereus*, *Streptococcus pneumoniae*, *Enterococcus faecalis*, or *Staphylococcus epidermidis*, and the gram-negative microorganisms may be *Salmonella typhimurium*, *Acinebacter calcoaceticus*, *Escherichia coli*, *Pseudomonas aeruginosa*, *Klebsiella aerogenes*, *Acinetobacter baumannii*, or *Klebsiella pneumoniae*, but the microorganisms are not particularly limited thereto.

In the present invention, "a microorganism of the genus *Staphylococcus*" refers to a microorganism which belongs to the genus *Micococcaceae* and the microorganism includes *Staphylococcus aureus*, *Staphylococcus epidermidis*, *Staphylococcus saprophyticus*, etc., and is called *Staphylococcus*. The microorganism of the genus *Staphylococcus* is present in the gastrointestinal tract, and additionally, in the skin or mucous membranes of humans or animals. Examples of the microorganisms isolated from people with diseases include *S. aureus*, *S. epidermidis*, *S. saprophyticus*, *S. haemolyticus*, *S. hominis*, *S. warneri*, etc. For the purpose of the present invention, the microorganism of the genus *Staphylococcus* may include any microorganism without limitation that can be used as a target of antimicrobial compounds provided in the present invention.

*Staphylococcus aureus*, an exemplary microorganism of the genus *Staphylococcus*, is a gram-positive facultative anaerobe which is generally present in the skin and on the nasal surface of healthy people or cattle. *Staphylococcus aureus* produces heat-resistant exotoxins which cause food poisoning and secretes a toxin (leukocidin), hemolysins, coagulase, etc., which kill phagocytes, and is thereby capable of escaping the resistance of the infected host cells and causing purulent infections. MRSA and QRSA, which are microorganisms recently reported to show a resistance to most antibiotic materials within hospitals, etc., also belong to *Staphylococcus aureus*.

Additionally, *Staphylococcus epidermidis*, an exemplary microorganism of the genus *Staphylococcus*, is a gram-positive bacterium and can cause sepsis, urinary tract infection, endocarditis, etc. In this regard, since the composition can cause the apoptosis of the microorganisms that belong to the genus *Staphylococcus*, the above diseases caused by a microorganism of the genus *Staphylococcus* can be treated using the composition.

In the present invention, "a microorganism of the genus *Bacillus*" is a collective term referring to rod-shaped bacteria. In general, the microorganism is present in various environments in nature such as living environments of people, soils, etc. About 148 species are known at present and some are known to cause food poisoning. For the purpose of the present invention, the microorganism of the genus *Bacillus* can include without limitation any microorganism that can be used as a target of antimicrobial compounds provided in the present invention. In the present invention, the microorganism of the genus *Bacillus* may be specifically *Bacillus subtilis* or *Bacillus cereus*, but is not limited thereto. In this regard, since the composition can cause the apoptosis of microorganisms that belong to the genus *Bacillus*, the above disease caused by a microorganism of the genus *Bacillus* can be treated using the composition.

In the present invention, "a microorganism of the genus *Streptococcus*" is a gram-positive microorganism of the genus *Streptococcaceae* and it is one of the pathogens causing pyogenic infection, etc. For the purpose of the present invention, the microorganism of the genus *Streptococcus* can include without limitation any microorganism that can be used as a target of antimicrobial compounds provided in the present invention.

The *Streptococcus pneumoniae* is a gram-positive diplococcus and it is a pathogen causing pneumonia, pleural empyema, tympanitis, mastoiditis, bacteremia. meningitis, osteomyelitis, arthritis, peritonitis, pericarditis, cellulitis, etc. In this regard, since the composition can cause the apoptosis of microorganisms that belong to the genus *Streptococcus*, the above diseases caused by a microorganism of the genus *Streptococcus* can be treated using the composition.

In the present invention, "a microorganism of the genus *Salmonella*" is a gram-negative microorganism and is one of the pathogens causing typhus, acute gastroenteritis, food poisoning, etc. For the purpose of the present invention, the microorganism of the genus *Salmonella* can include without limitation any microorganism that can be used as a target of antimicrobial compounds provided in the present invention. In the present invention, the microorganism of the genus *Salmonella* may be specifically *Salmonella typhimurium*, but is not limited thereto. In this regard, since the composition can cause the apoptosis of microorganisms that belong to the genus *Salmonella*, the above diseases caused by a microorganism of the genus *Salmonella* can be treated using the composition.

For the purpose of the present invention, a microorganism of the genus *Acinebacter* may include any microorganism without limitation that can be used as a target of antimicrobial compounds provided in the present invention. In the present invention, the microorganism of the genus *Acinetobacter* may be specifically *Acinetobacter baumannii*, but is not limited thereto. The *Acinetobacter baumannii* is a gram-negative microorganism and it is a multidrug-resistant microorganism having a resistance to fluoroquinolone antibiotics, carbapenem antibiotics, and aminoglycoside antibiotics. In this regard, since the composition can cause the apoptosis of microorganisms that belong to the genus *Acinetobacter*, the above diseases caused by a microorganism of the genus *Acinetobacter* can be treated using the composition.

In the present invention, "a microorganism of the genus *Escherichia*" is a gram-negative microorganism and is a kind of enterobacteria and a pathogen causing food poisoning, etc. For the purpose of the present invention, a microorganism of the genus *Escherichia* may include any microorganism without limitation that can be used as a target of antimicrobial compounds provided in the present invention. In the present invention, the microorganism of the genus *Escherichia* may be specifically *Escherichia coli*, but is not limited thereto. In this regard, since the composition can cause the apoptosis of microorganisms that belong to the genus *Escherichia*, the above diseases caused by a microorganism of the genus *Escherichia* can be treated using the composition.

In the present invention, "a microorganism of the genus *Pseudomonas*" is a gram-negative microorganism, and the microorganism may be a pathogen or putrefactive bacteria, or may be used for the preparation of amino acids by amino acid fermentation. For the purpose of the present invention, a microorganism of the genus *Pseudomonas* may include any microorganism without limitation that can be used as a target of antimicrobial compounds provided in the present invention. *Pseudomonas aeruginosa*, an exemplary microorganism of the genus *Pseudomonas*, may cause bacteremia, sepsis, etc. In this regard, since the composition can cause the apoptosis of microorganisms that belong to the genus *Pseudomonas*, the above diseases caused by a microorganism of the genus *Pseudomonas* can be treated using the composition.

In the present invention, "a microorganism of the genus *Klebsiella*" is a gram-negative microorganism and it is a kind of enterobacteria. The microorganism of the genus *Klebsiella* can cause pneumonia, endocarditis, peritonitis, cholecystitis, urinary tract infection, sepsis, etc. For the purpose of the present invention, a microorganism of the genus *Klebsiella* may include any microorganism without limitation that can be used as a target of antimicrobial compounds provided in the present invention. In the present invention, the microorganism of the genus *Klebsiella* may be specifically *Klebsiella aerogenes*, or *Klebsiella pneumoniae* but is not limited thereto. In this regard, since the composition can cause the apoptosis of microorganisms that belong to the genus *Klebsiella*, the above diseases caused by a microorganism of the genus *Klebsiella* can be treated using the composition.

Additionally, in a specific embodiment of the present invention, the antimicrobial activities of coralmycin A against *Staphylococcus aureus*, MRSA, QRSA, VRE, VISA, *Bacillus subtilis*, *Bacillus cereus*, *Streptococcus pneumoniae*, *Enterococcus faecalis*, and *Staphylococcus epidermidis*, i.e., gram-positive microorganisms, were confirmed (Example 5). Additionally, it was confirmed that coralmycin B has an antimicrobial activity against *Staphylococcus aureus*, MRSA, *Streptococcus pneumoniae*, and *Enterococcus faecalis*, i.e., gram-positive microorganisms.

Additionally, in a specific embodiment of the present invention, the antimicrobial activities of coralmycin A against *Salmonella typhimurium*, *Acinetobacter calcoaceticus*, *Escherichia coli*, *Pseudomonas aeruginosa*, and *Klebsiella aerogenes*, i.e., gram-negative microorganisms, were confirmed (Example 5). Additionally, it was confirmed that coralmycin B has an antimicrobial activity against *E. coli*, *Pseudomonas aeruginosa*, *Acinetobacter baumannii*, and *Klebsiella pneumoniae*, i.e., gram-negative microorganisms.

The antimicrobial composition of the present invention may be a pharmaceutical composition, a quasi-drug composition, a food composition, or a feed composition for livestock or fish, but is not limited thereto.

Specifically, the antimicrobial composition of the present invention may be a pharmaceutical composition for preventing or treating at least one disease selected from the group consisting of (i) to (iii) below:

(i) pyogenic infection;

(ii) food poisoning; and (iii) bacteremia, sepsis, urinary tract infection, pneumonia, pleural empyema, tympanitis, mastoiditis, meningitis, osteomyelitis, arthritis, peritonitis, pericarditis, cellulitis, typhus, and acute gastroenteritis, but is not limited thereto.

As described above, coralmycins A and B of the present invention have very strong antimicrobial activities against the microorganisms of the genus *Staphylococcus*, the genus *Bacillus*, the genus *Streptococcus*, the genus *Enterococcus*, the genus *Salmonella*, the genus *Acinetobacter*, the genus *Escherichia*, the genus *Pseudomonas*, and the genus *Klebsiella*, which cause pyogenic infection, food poisoning, bacteremia, sepsis, urinary tract infection, pneumonia, pleural empyema, tympanitis, mastoiditis, meningitis, osteomyelitis, arthritis, peritonitis, pericarditis, cellulitis, typhus, acute gastroenteritis, etc. Therefore, it is obvious that coralmycins A and B of the present invention can be used for the prevention or treatment of the diseases described above. Additionally, it will be obvious to a person of ordinary skill in the art that the effects of preventing or treating the above diseases may be exhibited not only by coralmycins A and B but also by a microorganism of the genus *Corallococcus* producing these compounds, spores of the microorganism, a culture broth of the microorganism, an extract of the microorganism, a fraction of the extract, or a mixture thereof.

As used herein, the term "pyogenic infection" is a symptom caused by bacteria such as *Staphylococcus aureus* and is divided according to the infected tissues or causative pathogens. In the present invention, pyogenic infection may be one among tympanitis, cystitis, pyogenic acne, furuncle, carbuncle, cellulitis, whitlow, and lymphangitis, but is not limited thereto.

Additionally, the pharmaceutical composition of the present invention may further contain an appropriate carrier, excipient, and diluent which are conventionally used in the preparation of pharmaceutical compositions. According to the conventional methods, each of the pharmaceutical composition of the present invention may be formulated into oral formulations such as powders, granules, tablets, capsules, suspensions, emulsions, syrups, aerosols, etc.; formulations for external use; suppositories; and sterile injection solutions for use. In the present invention, examples of the carrier, excipient, and diluent to be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, etc. For formulation, commonly used fillers, extenders, binders, humectants, disintegrants, diluents such as surfactants or excipients may be used. Examples of solid formulations for oral administration may include tablets, pills, powders, granules, capsules, etc. These solid formulations are prepared, for example, by addition at least one excipient (e.g., starch, calcium carbonate, sucrose, lactose, gelatin, etc) to the extract of red beans and fractions thereof. Additionally, lubricants such as magnesium stearate, talc, etc., may be used in addition to the simple excipients. Examples of liquid preparations for oral administration include suspensions, oral solutions, emulsions, syrups, etc., and various kinds of excipients (e.g., humectants, sweeteners, fragrances, preservatives, etc.) may be used in addition to simple diluents such as water and liquid paraffin. Preparations for parenteral administration include sterile aqueous solutions, non-aqueous solvents, suspensions, emulsions, lyophilized preparations, and suppositories. Examples of non-aqueous solvents, suspensions may include propylene glycol, polyethylene glycol, a vegetable oil such as olive oil, an injectable ester such as ethylolate, etc. Examples of suppository bases include Witepsol, Macrogol, Tween 61, cacao butter, laurinum, glycerogelatin, etc.

The pharmaceutical composition may be administered in a pharmaceutically effective amount.

As used herein, the term "a pharmaceutically effective amount" refers to an amount sufficient for the treatment of a disease at a reasonable benefit/risk ratio but without any adverse effects, thereby being applicable to medical treatment. The level of the effective dose may be easily determined by the health status of a patient, type of a disease, severity of a disease, drug activities, drug sensitivities, methods of administration, duration of administration, routes of administration and excretion rate, duration of treatment, factors including drugs used at the same time or in combination, and other factors well-known in the medical field. The composition of the present invention may be administered as an individual therapeutic agent or in combination with other therapeutic agent(s). The composition of the present invention may be administered sequentially or simultaneously along with the conventional therapeutic agent(s), and may be administered as a single-dose or multi-dose administration. It is important that the administration dose be in a minimal amount to obtain the maximal effect without adverse effects considering the factors described above, and these factors can be easily determined by one of ordinary skill in the art. Specifically, the composition of the present invention may be administered in the amount of 0.1 mg/kg to 50 mg/kg of body weight, and more preferably 5 mg/kg to 30 mg/kg of body weight.

As used herein, the term "administration" refers to provision of a particular material to a patient using any suitable method and the pharmaceutical composition of the present invention may be administered by any of the conventional routes, as long as it enables the delivery of the composition to the target tissue. The pharmaceutical composition of the present invention may be administered by intraperitoneal, intravenous, intramuscular, subcutaneous, intradermal, oral, local, intranasal, intrapulmonary, or intrarectal administration, but is not limited thereto. Additionally, the pharmaceutical composition of the present invention may be administered using any device that can transport an active material to a target cell.

In the present invention, the term "subject" may refer to all animals including humans, monkeys, cows, horses, sheep, pigs, chickens, turkeys, quails, cats, dogs, mice, rats, rabbits, or guinea pigs, which have or are at the risk of developing the above disease. The above disease can be effectively prevented or treated by administering the pharmaceutical composition of the present invention to a subject.

Specifically, in the present invention, the antimicrobial composition may be a quasi-drug composition, but is not limited thereto. As described above, the antimicrobial composition of the present invention has a very strong antimicrobial activity against microorganisms of the genus *Staphylococcus*, the genus *Bacillus*, the genus *Streptococcus*, the genus *Enterococcus*, the genus *Salmonella*, the genus *Acinetobacter*, the genus *Escherichia*, the genus *Pseudomonas*, and the genus *Klebsiella*, and thus it can be used as an antimicrobial quasi-drug composition.

As used herein, the term "quasi-drugs" refers to any of the products corresponding to fiber or rubber products or analogs thereof that are used for the treatment, alleviation, handling, or prevention of diseases in humans or animals; products other than instruments and machines, and analogs thereof which have a weak action in humans or do not directly act in human body; products corresponding to any of the germicides or insecticides, and analogs thereof for the prevention of epidemics, other than instruments, machines, and apparatuses that are used for the diagnosis, treatment, alleviation, handling, or prevention of diseases in humans or animals, and products excluding those other than instruments, machines, and apparatuses that are used for providing pharmacological effects on the structures and functions of humans or animals; and external skin preparations and personal hygiene products are also included therein.

When the compounds represented by Formula 1 or Formula 2 of the present invention are added into a quasi-drug composition for the antimicrobial purpose, the compounds represented by Formula 1 or 2 may be added as they are or used in combination with other quasi-drug ingredients, and may be appropriately used according to the conventional method. The mixed amounts of the active ingredients may be appropriately determined according to their intended purposes.

Specifically, the external skin preparations may be prepared in the form of ointments, lotions, sprays, patches, creams, powders, suspensions, gelling agents, or gels, but are not particularly limited thereto. Specifically, the personal hygiene products may be soaps, cosmetics, wet tissues, toilet paper rolls, shampoos, skin creams, facial creams, toothpastes, lipsticks, make-ups, foundations, blushers, mascaras, eye shadows, sunscreen lotions, haircare products, air-freshener gels, or facial cleansing gels, but are not particularly limited thereto. Additionally, other examples of the quasi-drugs of the present invention may include disinfectants, shower foams, mouthwash products, wet tissues, detergents, handwashes, humidifier fillers, masks, ointments, or filter fillers.

Specifically, the antimicrobial composition of the present invention may be a food composition, but is not limited thereto.

As described above, the coralmycins A and B of the present invention have strong antimicrobial activities against the microorganisms of the genus *Staphylococcus*, the genus *Bacillus*, the genus *Streptococcus*, the genus *Enterococcus*, the genus *Salmonella*, the genus *Acinetobacter*, the genus *Escherichia*, the genus *Pseudomonas*, and the genus *Klebsiella*, and thus it is obvious that these compounds can be used in the antimicrobial food composition. Additionally, it is obvious to one of ordinary skill in the art that not only coralmycins A and B but also spores of the microorganism which produce these compounds, a culture broth of the microorganism, an extract of the microorganism, or a fraction of the extract can also exhibit a antimicrobial activity, and thus these can be used in the antimicrobial food composition.

As used herein, the term "food" includes meats, sausages, breads, chocolates, candies, snacks, cookies, pizzas, ramens, other noodles, gums, dairy products including ice creams, various kinds of soups, beverages, teas, drinks, alcoholic beverages, vitamin complexes, etc., and all kinds of foods in the conventional meaning are included.

As used herein, the term "functional food" is the same term as food for special health use (FoSHU), and it refers to a food having high medical and medicinal effects processed to exhibit biological regulation function with efficiency, in addition to nutrition supply. As used herein, in comparison to general food, the term "health food" refers to a food which has active effects of maintaining or promoting health, and the term "health supplement food" refers to a food with a health supplementary purpose. Often, the terms functional food, health food, and health supplement food are used interchangeably. The foods may be prepared in various forms including tablets, capsules, powders, granules, liquids, pills, etc.

Compounds represented by Formula 1 or 2 above, an isomer thereof, a derivative thereof, or a pharmaceutically acceptable salt thereof, a microorganism of the genus *Corallococcus* producing the same, spores of the microorganism, a culture broth of the microorganism, an extract of the microorganism, a fraction of the extract, or a mixture thereof may be contained in an amount of 0.01 wt % to 100 wt % based on the total weight of a food composition, and more specifically, 1 wt % to 80 wt %. In a case when the food is beverage, the composition may be contained in an amount of 1 g to 30 g, specifically 3 g to 20 g based on 100 mL of the beverage, but is not limited thereto.

Additionally, the composition may further contain an ingredient that can be used to improve smell, taste, vision, etc. For example, vitamins A, C, D, E, B1, B2, B6, B12, niacin, biotin, folate, panthotenic acid, etc., may be contained. Additionally, minerals such as Zn, Fe, Ca, Cr, Mg, Mn, Cu, Cr, etc., may be contained. Additionally, amino acids such as lysine, tryptophan, cysteine, valine, etc., may be contained. Additionally, food additives such as a preservative (potassium sorbate, sodium benzoate, salicylic acid, sodium dehydroacetate, etc.), a germicide (bleaching powder, high-grade bleaching powder, sodium hydrochlorite, etc.), an antioxidant (butylhydroxyanisole (BHA), butylhydroxytoluene (BHT), etc.), a colorant (tar dye, etc.), a color fixing agent (e.g., sodium nitrate, sodium nitrite, etc.), a bleaching agent (sodium sulfite), a seasoning agent (e.g., MSG, sodium glutamate, etc.), a sweetener (e.g., dulcin, cyclamate, sodium saccharine, etc.), a flavoring agent (vanillin, lactone, etc.), a blowing agent (alum, potassium D-bitartrate, etc.), a fortifying agent, an emulsifying agent, a thickener (thickening agent), a coating agent, a gum base, an antifoaming agent, a solvent, and an improving agent may be contained. The additives may be selected according to food types, and they may be used in suitable amounts.

Specifically, in the present invention, the antimicrobial composition may be a feed composition for cattle or fish, but is not limited thereto.

The amounts of compounds contained in the feed composition for cattle or fish of the present invention represented by Formula 1 or 2 above, an isomer thereof, a derivative thereof, or a pharmaceutically acceptable salt thereof, a microorganism of the genus *Corallococcus*, spores of the microorganism, a culture broth of the microorganism, an extract of the microorganism, a fraction of the extract, or a mixture thereof may vary depending on the purposes and conditions of use, for example, may be contained in an amount of 0.01 wt % to 100 wt %, and more specifically, in an amount of 1 wt % to 80 wt % based on the total weight of the feed composition for cattle or fish.

Additionally, the feed composition may be prepared into coarse or granular materials with light viscosity according to the degree of pulverization of its ingredients. The feed composition may be supplied in a mesh or formed into a desired separate shape for further processing or packaging, or may undergo pelletization, expansion, or extrusion processes for storage purposes, and specifically for the easiness of storage, an excess amount of water may be removed by drying.

Another aspect of the present invention provides a method for treating at least one disease selected from the group consisting of (i) to (iii) below, including administering the antimicrobial composition to a subject in need thereof:
 (i) pyogenic infection;
 (ii) food poisoning; and
 (iii) bacteremia, sepsis, urinary tract infection, pneumonia, pleural empyema, tympanitis, mastoiditis, meningitis, osteomyelitis, arthritis, peritonitis, pericarditis, cellulitis, typhus, and acute gastroenteritis.

As described above, the antimicrobial composition has very strong antimicrobial activities against antibiotic-resistant microorganisms and multidrug-resistant microorganisms as well as against gram-positive and gram-negative microorganisms, and thus the composition can be used for the treatment of various microbial infections.

Still another aspect of the present invention provides a method for preparing compounds represented by Formula 1 or 2 above, an isomer thereof, a derivative thereof, or a pharmaceutically acceptable salt thereof, including:
 (a) Culturing a microorganism of the genus *Corallococcus*;
 (b) extracting a culture broth or fruiting body obtained in step (a); and
 (c) isolating the compounds represented by Formula 1 or 2 above, an isomer thereof, a derivative thereof, or a pharmaceutically acceptable salt thereof from the extract obtained in step (b).

Specifically, the microorganism may be a microorganism of *Corallococcus coralloides*, and more specifically, *Corallococcus coralloides* M23 microorganism with Accession No. of KCTC18279P, but is not limited thereto.

According to the preparation method of the present invention, the compounds represented by Formula 1 or 2 above, an isomer thereof, a derivative thereof, or a pharmaceutically acceptable salt thereof having strong antimicrobial activities may be prepared.

In the present invention, the microorganism of the genus *Corallococcus* for producing the compounds of the present invention may be cultured in medium containing nutrient sources that can be utilized by conventional microorganisms. As the nutrient sources for the microorganism, any nutrient source conventionally used in the art may be used without limitation, and specifically, known nutrient sources that are used in the conventional cultivation of fungi may be used. For example, glucose, starch syrup, dextrin, starch, molasses, animal oil, vegetable oil, etc., may be used as carbon sources; and wheat bran, soybean meal, wheat, malt, cottonseed meal, fish scrap, corn steep liquor, meat gravy, yeast extract, ammonium sulfate, sodium nitrate, urea, etc., may be used as nitrogen sources. The addition of table salt, potassium, magnesium, cobalt, chloride, phosphoric acid, sulfuric acid, and inorganic salts that promote ion production as necessary will make the cultivation more effective. Possible cultivation methods may include shake culture or stationary culture in an aerobic condition. Although the cultivation temperature may vary slightly according to conditions when cultured in each of the above conditions, normally it is appropriate to culture at a temperature between 20° C. and 37° C., and specifically at a temperature between 26° C. and 30° C. Additionally, the cultivation may also be performed for a known period of time used in the art and the period may be adjusted as necessary.

Since the compounds of the present invention can be present not only in the culture medium but also within fruiting bodies, the above compounds can be extracted from the medium or fruiting bodies.

The extraction and isolation method of the compounds may be performed by the methods conventionally used in the art without limitation, and it is obvious that the amount and efficiency of the compounds as products can be controlled by changing the type of medium, cultivation conditions, extraction/purification methods, etc., as necessary.

In a specific embodiment of the present invention, the amberlite XAD16 (Aldrich XAD16) was recovered in the culture broth of a *Corallococcus coralloides* M23 microorganism (Example 2); active ingredients were extracted from the amberlite XAD16 by stirring after adding acetone thereto; a solvent extraction was performed with ethyl acetate after evaporating acetone; the ethyl acetate solvent layer including the active ingredients was concentrated under reduced pressure to remove ethyl acetate; and the resultant was subjected to Sephadex LH-20 column chromatography; and thereby the pure materials of the present invention were obtained (Example 3). The inventors have confirmed that the use of the above method enables effective extraction and isolation of coralmycins A and B from the *Corallococcus coralloides* M23 microorganism.

Still another aspect of the present invention provides the uses of the above compounds for preparing a pharmaceutical drug for the treatment of at least one disease selected from the group consisting of (i) to (iii) below, an isomer thereof, a derivative thereof, or a pharmaceutically acceptable salt thereof, a microorganism of the genus *Corallococcus* producing the same, spores of the microorganism, a culture broth of the microorganism, an extract of the microorganism, a fraction of the extract, or a mixture thereof:

(i) pyogenic infection;
(ii) food poisoning; and
(iii) bacteremia, sepsis, urinary tract infection, pneumonia, pleural empyema, tympanitis, mastoiditis, meningitis, osteomyelitis, arthritis, peritonitis, pericarditis, cellulitis, typhus, and acute gastroenteritis.

Specifically, the microorganism may be *Corallococcus coralloides*, and more specifically, a *Corallococcus coralloides* M23 microorganism with the Accession Number of KCTC18279P, but is not limited thereto.

The compounds of the present invention, an isomer thereof, a derivative thereof, or a pharmaceutically acceptable salt thereof, a microorganism of the genus *Corallococcus* producing the same, spores of the microorganism, a culture broth of the microorganism, an extract of the microorganism, a fraction of the extract, or a mixture thereof have very strong antimicrobial activities against antibiotic-resistant microorganisms and multidrug-resistant microorganisms as well as against gram-positive and gram-negative microorganisms, and thus the compounds of the present invention can be used in the preparation of pharmaceutical drugs for treating the above diseases.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1: Isolation and Identification of Microorganisms

A *Corallococcus coralloides* M23 microorganism with Accession No. of KCTC18279P was isolated from a soil sample collected from the brook located at Imhakdong-ro, Incheon, Korea according to the method reported by Park et al. (S. Park, B. Lee, J. Kim, C. Lee, E. Jang and K. Cho, *Kor. J. Microbiol. Biotechnol.* 32: 218, 2004).

For the identification of the *Corallococcus coralloides* M23 microorganism, physiological and morphological tests were performed. As a result, it was confirmed that the M23 microorganism is a gram-negative *Bacillus* with a length of about 4 μm (FIG. 1A), which showed vegetative growth feeding on *E. coli*, and migrated with gliding motility. Additionally, the microorganism formed its unique fruiting bodies in WC medium (10 mM 3[N-morpholino]propanesulfonic acid (pH 7.6), 0.1% $CaCl_2 \cdot 2H_2O$, 1.5% agar) (FIG. 1B).

In order to perform the identification of microorganisms based on the nucleotide sequence of 16S rDNA, the M23 microorganism was cultured in CY medium and the DNA of the microorganism was extracted. The DNA was amplified by performing PCR for 30 cycles using primers 27F (5'-GAGTTTGATCCTGGCTCAG-3'; SEQ ID NO: 1) and 1544R (5'-AGAAAGGAGGTGATCCAGCC-3'; SEQ ID NO: 2) in conditions of 94° C. for 30 sec, 55° C., for 30 sec, and 72° C. for 2 min), purified, and sequence analysis thereof was requested from Macrogen Inc. As a result, it was confirmed that the 16S rDNA nucleotide sequence of the *Corallococcus coralloides* M23 microorganism showed a similarity of 99.86% to the 16S rDNA nucleotide sequence of the *Corallococcus coralloides* standard microorganism (DSM 2259(T)). Accordingly, the M23 microorganism was identified as a novel microorganism belonging to *Corallococcus coralloides* based on the physiological and morphological characteristics and analysis of 16S rDNA nucleotide sequence, and the M23 microorganism was deposited to the Korean Collection for Type Culture (KCTC) located at 125 Gwahak-ro, Yuseong-gu, Daejeon, Korea, on Apr. 2, 2014, and assigned Accession No. KCTC18279P. Additionally, the microorganism (Accession No. KCTC18279P) was deposited to the KCTC, which is an international depository authority under the Budapest Treaty and assigned the Accession Number of KCTC12812BP. Therefore, the Accession Nos. KCTC18279P and KCTC12812BP can be used interchangeably in the present invention.

Example 2: Cultivation of Microorganisms

The surface of a piece of a filter paper, on which the spores of the *Corallococcus coralloides* M23 microorganism were present, was spread on the entire surface of VY/3 medium (0.5% Baker's yeast, 0.1% $CaCl_2.2H_2O$, 10 mM MOPS (pH 7.6), 1.5% bacto-agar, 0.5 ppm cyanocobalamine). After wrapping, the medium was cultured for about 10 days until the formation of fruiting bodies was confirmed at 28° C.

CYS medium (0.5% casitone, 0.1% yeast extract, 0.3% soluble starch, 0.1% $MgSO_4.7H_2O$, 0.05% $CaCl_2$, 50 mM HEPES (pH 7.6)) in an amount of 100 mL was added to a 500 mL Erlenmeyer flask, sterilized, and then an ST-trace element solution (0.01% $MnCl_2.4H_2O$, 0.004 $CoCl_2.6H_2O$, 0.0016% $CuSO_4.5H_2O$, 0.001% $Na_2MoO_4.2H_2O$, 0.002% $ZnCl_2$, 0.0005% LiCl, 0.0005% $SnCl_2.2H_2O$, 0.001% $H_3BO_3$, 0.002% KBr, 0.002% KI, 0.08% EDTA Na—$Fe^{3+}$ salt (trihydrate)) and a vitamin B12 solution (0.05% cyanocobalamine) in an amount of 100 mL, respectively, were added to the sterilized CYS medium. Then, a microorganism cultured in VY/3 medium was added into the flask in an amount of a ¼ piece per flask and cultured at 28° C. at a rate of 180 rpm for 3 days.

CYS medium (250 mL) was added into a 1 L Erlenmeyer flask, sterilized, and then the ST-trace element solution and vitamin B12 solution in an amount of 250 mL, respectively, and sterilized amberlite XAD16 (Aldrich XAD16) in an amount of 4 mL were added thereto. Then, the culture solution, obtained by culturing for 3 days, was inoculated in an amount of 25 mL, respectively, and cultured at 28° C. at a rate of 150 rpm for 9 days.

Example 3: Isolation and Purification of Coralmycins

After the cultivation in Example 2, the amberlite XAD16 in the culture solution was recovered. Acetone was added to the amberlite XAD16 and the mixture was stirred to extract active ingredients from the amberlite XAD16. After evaporating acetone, the extract was extracted 3 times by solvent extraction using ethyl acetate. The thus-obtained ethyl acetate solvent layer containing active ingredients was concentrated under reduced pressure to remove ethyl acetate and the resulting residue was subjected to Sephadex LH-20 column chromatography using methanol as a solvent. The thus-obtained active fraction was concentrated under reduced pressure and then subjected to HPLC, in a condition where methanol:water is 50:50, to obtain compounds 1 and 2 of the active fraction.

Example 4: Analysis of Physicochemical Characteristics of Coralmycins

The compounds 1 (coralmycin A) and 2 (coralmycin B) obtained in Example 2 were analyzed spectroscopically using $^{13}C$ NMR and high resolution ESI-MS (Table 1).

TABLE 1

| Position | Coralmycin A (DMSO-$d_6$) $\delta_H$ (J, Hz) | $\delta_C$ | Coralmycin A (CD$_3$OD) $\delta_H$ (J, Hz) | $\delta_C$ | Coramycin B (CD$_3$OD) $\delta_H$ (J, Hz) | $\delta_C$ |
|---|---|---|---|---|---|---|
| 1 |  | 166.9 |  | 170.5 |  | 175.6 |
| 2 |  | 125.7 |  | 128.3 |  | 117.0 |
| 3 | 7.56 (1H, brs) | 113.9 | 7.68 (1H, brs) | 115.2 |  | 156.1 |
| 4 |  | 146.3 |  | 148.5 |  | 136.2 |
| 5 |  | 133.3 |  | 134.1 |  | 137.0 |
| 6 | 8.50 (1H, d, 8.3) | 119.6 | 8.48 (1H, d, 8.8) | 121.5 | 7.81 (1H, d, 9.0) | 111.3 |
| 7 | 7.58 (1H, d, 8.3) | 122.6 | 7.67 (1H, d, 8.8) | 124.1 | 7.63 (1H, d, 9.0) | 126.4 |
| 8 | 4.75 (1H, m) | 71.7 | 4.78 (1H, m) | 73.4 | 4.80 (1H, m) | 75.9 |
| 9, 10 | 1.37 (6H, d, 6.0) | 21.6 | 1.46 (6H, d, 6.1) | 22.2 | 1.33 (6H, d, 6.0) | 22.6 |
| 11 | 10.97 (1H, brs) |  |  |  |  |  |
| 1' |  | 163.6 |  | 167.0 |  | 167.0 |
| 2' |  | 116.4 |  | 117.2 |  | 116.9 |
| 3' |  | 150.3 |  | 153.2 |  | 153.1 |
| 3'-OH | 11.21 (1H, brs) |  |  |  |  |  |
| 4' |  | 138.4 |  | 139.1 |  | 138.9 |
| 5' |  | 136.2 |  | 137.8 |  | 137.5 |
| 6' | 7.50 (1H, d, 8.5) | 115.3 | 7.73 (1H, d, 8.3) | 115.4 | 7.74 (1H, d, 9.0) | 115.0 |
| 7' | 7.80 (1H, d, 8.5) | 124.9 | 7.79 (1H, d, 8.3) | 125.7 | 7.77 (1H, d, 9.0) | 125.4 |
| 8' | 4.32 (1H, m) | 75.6 | 4.53 (1H, m) | 77.4 | 4.55 (1H, m) | 77.2 |
| 9', 10' | 1.26 (6H, d, 6.1) | 22.0 | 1.35 (6H, d, 6.0) | 22.6 | 1.35 (6H, d, 6.0) | 22.6 |
| 11' | 9.58 (1H, s) |  |  |  |  |  |
| 1" |  | 164.3 |  | 167.3 |  | 167.1 |
| 2" |  | 128.6 |  | 131.0 |  | 131.0 |
| 3", 7" | 7.97 (2H, d, 8.6) | 128.4 | 7.97 (2H, d, 8.6) | 129.6 | 7.97 (2H, d, 8.8) | 129.5 |
| 4", 6" | 7.83 (2H, d, 8.6) | 118.8 | 7.84 (2H, d, 8.6) | 121.2 | 7.84 (2H, d, 8.8) | 121.2 |
| 5" |  | 142.1 |  | 143.5 |  | 143.4 |
| 8" | 10.56 (1H, s) |  |  |  |  |  |
| 1''' |  | 168.6 |  | 170.0 |  | 169.9 |
| 2''' | 4.92 (1H, t, 8.0) | 55.7 | 5.06 (1H, t, 8.0) | 57.7 | 5.08 (1H, t, 7.5) | 57.6 |
| 3''' | 4.09 (1H, d, 8.0) | 79.7 | 4.18 (1H, d, 8.0) | 82.5 | 4.18 (1H, d, 7.5) | 82.5 |
| 4''' |  | 170.8 |  | 174.8 |  | 174.7 |
| 4''' $NH_a$ | 7.47 (1H, brs) |  |  |  |  |  |
| $NH_b$ | 7.54 (1H, brs) |  |  |  |  |  |

TABLE 1-continued

| Position | Coralmycin A (DMSO-$d_6$) $\delta_H$ (J, Hz) | $\delta_C$ | Coralmycin A (CD$_3$OD) $\delta_H$ (J, Hz) | $\delta_C$ | Coramycin B (CD$_3$OD) $\delta_H$ (J, Hz) | $\delta_C$ |
|---|---|---|---|---|---|---|
| 5''' | 3.31 (3H, s) | 57.7 | 3.50 (3H, s) | 59.6 | 3.50 (3H, s) | 59.6 |
| 6''' | 8.46 (1H, d, 8.1) | | | | | |
| 1'''' | | 165.4 | | 169.4 | | 169.4 |
| 2'''' | | 128.9 | | 130.9 | | 130.9 |
| 3'''', 7'''' | 7.90 (2H, d)$^a$ | 128.2 | 7.92 (2H, d, 8.0) | 129.7 | 7.92 (2H, d, 9.0) | 129.7 |
| 4'''', 6'''' | 7.90 (2H, d)$^a$ | 119.6 | 7.89 (2H, d, 8.0) | 121.4 | 7.90 (2H, d, 9.0) | 121.3 |
| 5'''' | | 141.7 | | 143.5 | | 143.3 |
| 8'''' | 10.8 (1H, s) | | | | | |
| 1''''' | | 164.2 | | 167.0 | | 166.9 |
| 2''''' | | 140.4 | | 142.0 | | 141.8 |
| 3''''', 7''''' | 8.21 (2H, d, 8.6) | 129.3 | 8.16 (2H, d, 8.6) | 130.3 | 8.16 (2H, d, 8.8) | 130.2 |
| 4''''', 6''''' | 8.38 (2H, d, 8.6) | 123.5 | 8.38 (2H, d, 8.6) | 124.9 | 8.38 (2H, d, 8.8) | 124.7 |
| 5''''' | | 149.2 | | 151.9 | | 151.4 |
| 5''''' NO$_2$ | | | | | | |

$^a$overlapped signal

As a result, the $^1$H (500 MHz) and $^{13}$C (125 MHz) NMR spectroscopic data of compound 1, where dimethyl sulfoxide (DMSO-$d_6$) and methanol (CD$_3$OD) were used as solvents, and compound 2, where methanol (CD$_3$OD) was used as a solvent, are shown in Table 1 above.

From Table 1 above, it was confirmed that compounds 1 and 2 are novel compounds having the following physicochemical properties and were named as coralmycin A and coralmycin B, respectively.

1. Coralmycin A

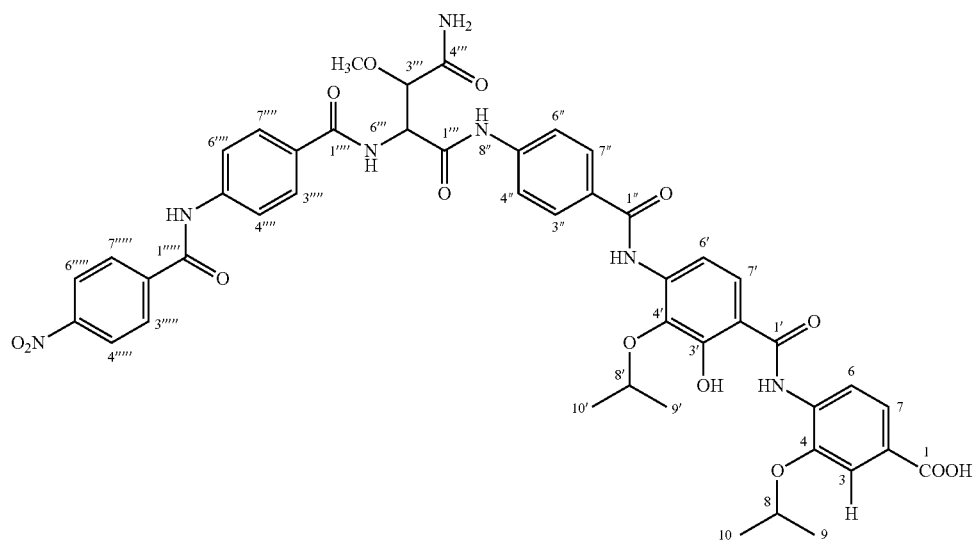 [SMILES: COC(C(N)=O)C(NC(=O)c1ccc(NC(=O)c2ccc([N+](=O)[O-])cc2)cc1)C(=O)Nc1ccc(C(=O)Nc2ccc(C(=O)Nc3ccc(C(=O)O)cc3OC(C)C)c(O)c2OC(C)C)cc1]

1) Images of Materials: white powder
2) Molecular Weight: 919
3) High-Resolution ESI-MS: experimental value; m/z 920.3083 (M+H)$^+$ (C$_{46}$H$_{45}$N$_7$O$_{14}$), calculated value; 920.3103
4) Molecular Formula: C$_{46}$H$_{45}$N$_7$O$_{14}$ 2. Coralmycin B

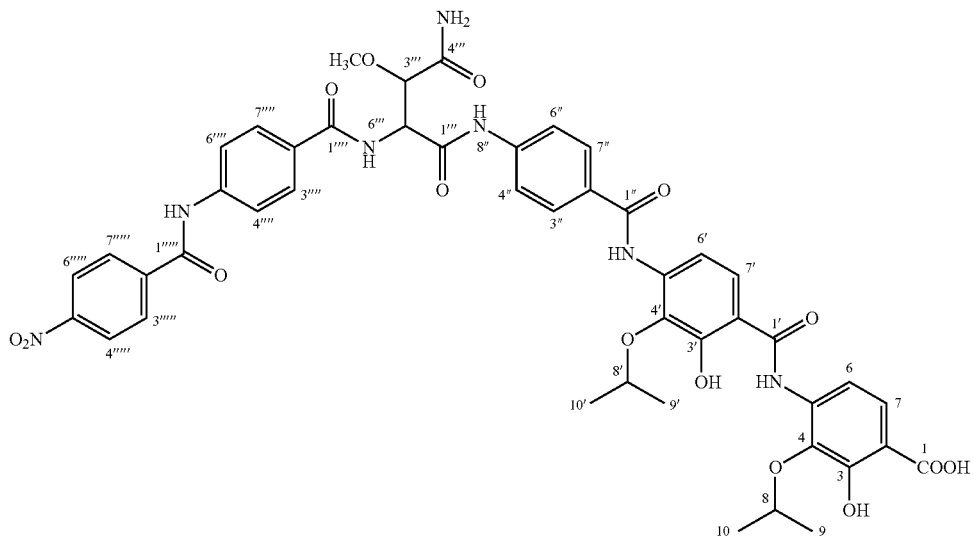 [SMILES: COC(C(N)=O)C(NC(=O)c1ccc(NC(=O)c2ccc([N+](=O)[O-])cc2)cc1)C(=O)Nc1ccc(C(=O)Nc2ccc(C(=O)Nc3ccc(C(=O)O)c(O)c3OC(C)C)c(O)c2OC(C)C)cc1]

1) Images of Materials: white powder
2) Molecular Weight: 935
3) High-Resolution ESI-MS: experimental value; m/z 934.2902 (M–H)$^-$ (C$_{46}$H$_{45}$N$_7$O$_{15}$), calculated value; 934.2895
4) Molecular Formula: C$_{46}$H$_{45}$N$_7$O$_{15}$ Example 5: Antimicrobial Activities of Coralmycin A A test microorganism was cultured in Mueller Hinton broth (MHB) and the antimicrobial activity was measured by the broth microdilution method. The test microorganism cultured overnight was diluted to a concentration of 2×100,000 cells/mL, aliquoted into a 96-well plate in a concentration of 100 mL per well, and the compound was treated on the well plate in concentrations starting from the highest concentration of 128 µg/mL to 2-fold gradually-diluted concentrations. The compound was diluted in dimethyl-sulfoxide (DMSO) and the experiment was performed by adjusting the DMSO concentration to a 1/100 level. After culturing for 20 hours, the OD value was measured at 650 nm and the growth of the microorganism was examined. The minimal concentration of the compound which completely inhibited the growth of the microorganism was determined as MIC.

The results are shown in Table 2 below.

TABLE 2

| Test Microorganisms | MIC (µg/mL) Coralmycin A |
| --- | --- |
| Staphylococcus aureus 503 | 1 |
| Staphylococcus aureus 209 | 0.125 |
| Staphylococcus aureus RN 4220 | 0.063 |
| MRSA CCARM 3167 | 0.125 |
| MRSA CCARM 3506 | 0.25 |

TABLE 2-continued

| Test Microorganisms | MIC (µg/mL) Coralmycin A |
| --- | --- |
| QRSA CCARM 3505 | 1 |
| QRSA CCARM 3519 | 1 |
| Bacillus subtilis KCTC 1021 | 0.063 |
| Bacillus subtilis KTCT 1661 | 0.125 |
| Streptococcus pneumoniae KTCT 5412 | 2 |
| Enterococcus faecalis KTCT 5191 | 0.125 |
| Enterococcus faecalis KTCT 3511 | 0.125 |
| Staphylococcus epidermidis KTCT 3958 | 0.125 |
| Salmonella typhimurium KTCT 1926 | 0.063 |
| Acinetobacter calcoaceticus KTCT 2357 | 0.25 |
| E. coli CCARM 1356 | 1 |
| E. coli KTCT 1682 | 0.5 |
| Pseudomonas aeruginosa KTCT 2004 | 8 |
| Pseudomonas aeruginosa KTCT 2742 | 32 |
| Klebsiella aerogenes KTCT 2619 | 8 |

The MIC of the coralmycin A compound in *S. aureus* was in a range of 0.06 µg/mL to 1 µg/mL. Additionally, the MICs of the coralmycin A compound in MRSA (CCARM3167, CCARM3506) and QRSA (CCARM 3505, CCARM 3519) were in a range of 0.1 µg/mL to 1 µg/mL. In particular, the MIC of the coralmycin A compound in *Escherichia coli* was in a range of 0.5 µg/mL to 1 µg/mL; 0.25 µg/mL in *Acinetobacter calcoaceticus*; and in a range of 8 µg/mL to 32 µg/mL in *Klebsiella aerogenes* and *Pseudomonas aeruginosa*.

From the above results, it was confirmed that coralmycin A has antimicrobial activities against microorganisms, which have a resistance to methicillin and quinolone antibiotics, and specifically, against methicillin-resistant *Staphylococcus aureus* (MRSA) and quinolone-resistant *Staphylococcus aureus* (QRSA).

Additionally, it was confirmed that coralmycin A has antimicrobial activities against gram-positive microorganisms, and specifically, against *Staphylococcus aureus*, methicillin-resistant *Staphylococcus aureus* (MRSA), quinolone-resistant *Staphylococcus aureus* (QRSA), *Bacillus* subtilis, Bacillus cereus, Streptococcus pneumoniae, Enterococcus faecalis, or Staphylococcus epidermidis.

Additionally, it was confirmed that coralmycin A has antimicrobial activities against gram-negative microorganisms, and specifically, against Salmonella typhimurium, Acinetobacter calcoaceticus, Escherichia coli, Pseudomonas aeruginosa, or Klebsiella aerogenes.

Additionally, the minimal concentration of the compounds coralmycin A and Triclosan (an antibiotic used as a control), which completely inhibited the growth of the microorganism, i.e., MICs, were measured and the results are shown in Table 3 below.

TABLE 3

| | MIC (µg/mL) | |
|---|---|---|
| Test Microorganisms | Triclosan | Coralmycin A |
| Bacillus subtilis KTCT 1661 | 2 | 0.125 |
| Streptococcus pneumoniae KTCT 5412 | 64 | 2 |
| Enterococcus faecalis KTCT 5191 | >64 | 0.125 |
| Enterococcus faecalis KTCT 3511 | >64 | 0.125 |
| Staphylococcus epidermidis KTCT 3958 | 0.25 | 0.125 |
| Acinetobacter calcoaceticus KTCT 2357 | >0.5 | 0.25 |
| Pseudomonas aeruginosa KTCT 2004 | >64 | 8 |
| Pseudomonas aeruginosa KTCT 2742 | >64 | 32 |

The coralmycin A compound showed a lower MIC compared to that of Triclosan, which was used as a control. In particular, the coralmycin A compound showed lower MICs, in a range of the minimal 8-fold to the maximal 128-fold, in Streptococcus pneumoniae, Enterococcus faecalis, Acinebacter calcoaceticus, and Pseudomonas aeruginosa compared to those of Triclosan. From these results, it was confirmed that coralmycin A or any microorganism producing coralmycin A has strong antimicrobial activities.

Example 6: Antimicrobial Activities of Coralmycin B

For the analysis of antimicrobial activities of coralmycin B, the antimicrobial activities of coralmycin B were measured in the same manner as in Example 5. Additionally, the minimal concentration of the coralmycin B compound which completely inhibited the growth of the microorganism was determined as MIC, and Ciprofloxacin was used as a control.

The results are shown in Table 4 below.

TABLE 4

| | MIC (µg/mL) | | |
|---|---|---|---|
| Test Microorganisms | Coralmycin A | Coralmycin B | Ciprofloxacin |
| Staphylococcus aureus RN 4220 | 0.063 | 0.015 | 0.125 |
| MRSA CCARM 3167 | 0.125 | 0.015 | 2 |
| Streptococcus pneumonia KCTC 5412 | 2 | 0.25 | 0.5 |
| Enterococcus faecalis KCTC 5191 | 0.125 | 0.03 | 0.5 |
| E. coli CCARM 1356 | 1 | 0.125 | 64 |
| E. coli KCTC 1682 | 0.5 | 0.125 | 0.003 |
| Pseudomonas aeruginosa KCTC 2004 | 8 | 4 | 0.06 |
| Acinetobacter baumannii KCTC 2508 | 0.25 | 0.125 | 0.125 |
| Klebsiella pneumoniae KCTC 22057 | 8 | 2 | 0.006 |

From the above results, it was confirmed that coralmycin B has antimicrobial activities against microorganisms, which have a resistance to methicillin antibiotics, specifically, against methicillin-resistant Staphylococcus aureus (MRSA), and multidrug-resistant microorganism, specifically, against Acinetobacter baumannii.

Additionally, it was confirmed that coralmycin B has antimicrobial activities against gram-positive microorganisms, and specifically, against Staphylococcus aureus, methicillin-resistant Staphylococcus aureus, Streptococcus pneumoniae, or Enterococcus faecalis.

Additionally, it was confirmed that coralmycin B has antimicrobial activities against gram-negative microorganisms, and specifically, against Escherichia coli, Pseudomonas aeruginosa, Acinetobacter baumannii, or Klebsiella aerogenes.

Additionally, it was confirmed that overall coralmycin B has a 2- to 8-fold higher antimicrobial activity compared to that of coralmycin A. It was also confirmed that coralmycin B has an at least about 133-fold higher antimicrobial activity in MRSA compared to that of ciprofloxacin, which is a commercially-available antibiotic; an at least about 16-fold higher antimicrobial activity in microorganisms of the genus Enterococcus faecalis; and an at least about 426-fold higher antimicrobial activity in Escherichia coli, thus confirming that coralmycin B has a very strong antimicrobial activity.

From the above results, it was confirmed that genus Corallococcus coralloides, which produce coralmycins A and B, has strong antimicrobial activities not only against gram-positive and gram-negative microorganisms but also against antibiotic-resistant and multidrug-resistant microorganisms, and thus genus Corallococcus coralloides can be very useful for prevention, treatment, and alleviation of various microbial infections, thereby enabling its wide applications in the medicine, quasi-drug, food, and feed industries.

Preparation Examples for the compositions of the present invention are provided herein below.

Preparation Example 1: Preparation of Pharmaceutical Formulations

Preparation Example 1-1. Preparation of Tablets

Tablets were prepared by a conventional method according to the following composition.

| | |
|---|---|
| coralmycin A or coralmycin B compound | 10.0 mg |
| lactose | 500.0 mg |
| talc | 5.0 mg |
| magnesium stearate | 1.0 mg |

Preparation Example 1-2. Preparation of Capsules

Capsules were prepared by a method according to the following composition. In particular, a gallamide derivative was sieved, mixed with an excipient, and filled into gelatin capsules to prepare capsules.

| | |
|---|---|
| coralmycin A or coralmycin B compound | 10.0 mg |
| starch 1500 | 10.0 mg |
| magnesium stearate | 100.0 mg |

Preparation Example 1-3. Preparation of Injections

Following ingredients were filled into ampoules (10.0 mL) and sterilized to prepare intramuscular injections by a conventional method for preparing injections.

| | |
|---|---|
| coralmycin A or coralmycin B compound | 10.0 mg |
| sodium bisulfite | 10.0 mg |
| methylparaben | 6.0 mg |
| propylparaben | 4.0 mg |
| monosodium phosphate | 12.0 mg |
| disodium phosphate | 8.0 mg |
| sodium hydroxide | 10.0 mg |
| injection water | 10.0 mL |

Preparation Example 2. Preparation of Quasi-Drug Formulations

Preparation Example 2-1. Preparation of Ointments

| | |
|---|---|
| coralmycin A or coralmycin B compound | 5.00 wt % |
| capric/caprylic triglyceride | 10.00 wt % |
| liquid paraffin | 10.00 wt % |
| sorbitan sesquioleate | 6.00 wt % |
| octyldodeceth-25 | 9.00 wt % |
| cetyl ethylhexanoate | 10.00 wt % |
| squalane | 1.00 wt % |
| salicylic acid | 1.00 wt % |
| glycerin | 15.00 wt % |
| sorbitol | 10.00 wt % |
| distilled water | the rest quantity wt % |

Preparation Example 2-2. Preparation of Lotions

The ingredients and contents of the lotions containing coralmycin A or B are shown below. Distilled water, triethanolamine, and butylene glycol, which are in an aqueous state, were dissolved by heating at 70° C. Then, a solution, which was prepared by dissolving fatty acids, oily ingredients, emulsifiers, and preservatives, which are in oily state, by heating at 70° C., was added thereto for emulsification. Upon completion of emulsification, 2% solution of xanthan gum, which is a hydrophilic thickener, was added thereto to a final concentration of 0.05 wt %. The solution was cooled to 45° C., and coralmycin A or B compound, fragrance(s), and colorant(s) were added thereto, mixed, and cooled to 30° C.

| | |
|---|---|
| coralmycin A or coralmycin B compound | 0.10 wt % |
| glycerin | 3.00 wt % |
| carbomer | 0.10 wt % |
| xanthan gum | 0.05 wt % |
| 1,3-butylene glycol | 3.00 wt % |
| polyglyceryl-3 methylglucose distearate | 1.50 wt % |
| glyceryl stearate | 0.50 wt % |
| cetylaryl alcohol | 0.30 wt % |
| jojoba oil | 3.00 wt % |
| liquid paraffin | 2.00 wt % |
| squalane | 3.00 wt % |
| dimethicone | 0.50 wt % |
| tocopheryl acetate | 0.20 wt % |
| triethanolamine | 0.10 wt % |
| preservative(s), fragrance(s), and colorant(s) | trace amount |
| distilled water | the rest quantity wt % |

Preparation Example 3. Preparation of Foods

Preparation Example 3-1. Preparation of Wheat Flour Foods

The coralmycin A or coralmycin B compound of the present invention in an amount of 0.5 to 5.0 parts by weight was added to flour and the mixture was used for the preparation of breads, cakes, cookies, crackers, and noodles.

Preparation Example 3-2. Preparation of Beverages

Inactive ingredients such as high fructose corn syrup (0.5%), oligosaccharides (2%), sugar (2%), table salt (0.5%), and water (75%), and the coralmycin A or coralmycin B compound of the present invention in an amount of 0.01% to 20% were mixed uniformly, sterilized instantly, and packed into small containers such as glass bottles and pet bottles, for the preparation of beverages.

Preparation Example 4. Preparation of Feeds for Cattle or Fish

Preparation Example 4-1. Preparation of Feeds for Pig Farming

| | |
|---|---|
| coralmycin A or coralmycin B compound | 0.15 wt % |
| corn | 42.66 wt % |
| rice | 9.99 wt % |
| fermented soybean meal | 3.52 wt % |
| soybean | 9.99 wt % |
| plasma protein(s) | 3.99 wt % |
| fish meal | 4.49 wt % |
| whey | 5.99 wt % |
| complex dairy product | 7.48 wt % |
| soybean oil | 2.49 wt % |
| amino acid premix | 0.49 wt % |
| feed additive premix | 4.22 wt % |
| acidifier premix | 2.2 wt % |
| others | 2.34 wt % |

Preparation Example 4-1. Preparation of Feeds for Fish

| | |
|---|---|
| coralmycin A or coralmycin B compound | 0.1 wt % |
| white fish meal | 52.0 wt % |
| soybean meal | 6.0 wt % |
| corn gluten meal | 6.0 wt % |
| wheat flour | 21.3 wt % |
| squid liver oil | 10.00 wt % |
| mineral premix | 1.0 wt % |
| vitamin premix | 1.0 wt % |
| choline chloride | 0.5 wt % |
| alanine | 1.1 wt % |
| cellulose | 1.0 wt % |

From the foregoing, a skilled person in the art to which the present invention pertains will be able to understand that the present invention may be embodied in other specific forms without modifying the technical concepts or essential characteristics of the present invention. In this regard, exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

What is claimed is:

1. A method of treating or alleviation a condition caused by a bacterial infection in a subject in need thereof, comprising:
administering to the subject an antibacterial composition comprising a compound represented by Formula 1 or Formula 2, or a pharmaceutically acceptable salt thereof, Formula 1

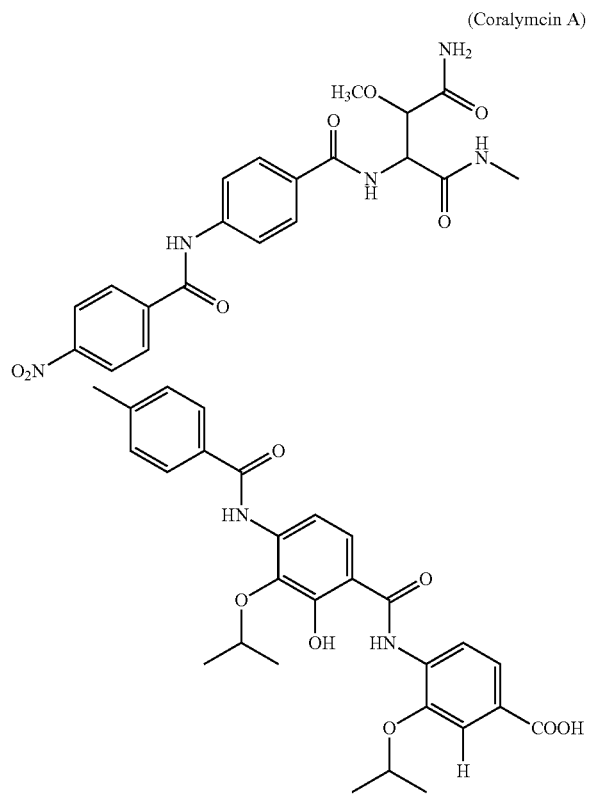

(Coralymcin A)

Formula 2

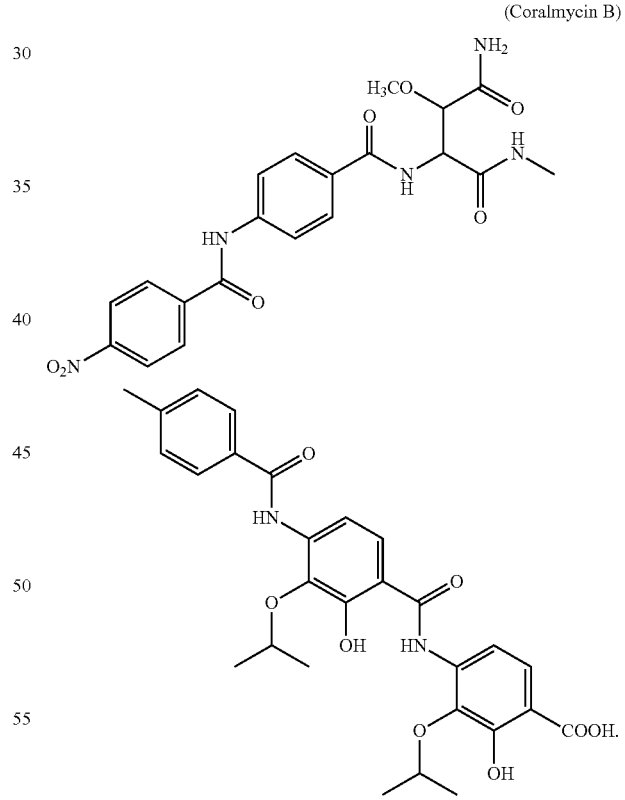

(Coralmycin B)

2. The method of claim 1, wherein the antibacterial composition further comprises a carrier, an excipient, a diluent, an additive, or combinations thereof.

3. The method of claim 1, wherein the antibacterial composition further comprises at least one component selected from the group consisting of methyl cellulose, polyvinyl pyrrolidone, magnesium stearate, polyethylene glycol, sodium dehydroacetate, sodium hypochlorite, butylhydroxyanisole (BHA), tar dye, dulcin, cyclamate and sodium saccharine.

4. The method according to claim 1, wherein the bacterial infection is an infection caused by a gram-negative microorganism.

5. The method of claim 1, wherein the bacterial infection is an infection caused by a bacteria having antibiotics resistance.

6. The method of claim 5, where in the antibiotics resistance is a resistance to at least one component selected from the group consisting of a penicillin antibiotic, a methicillin antibiotic, a quinolone antibiotic, a vancomycin antibiotic, a carbapenem antibiotic, and an aminoglycoside antibiotic.

7. The method of claim 1, wherein the bacterial infection is the infection caused by at least one gram-positive microorganism selected from the group consisting of the genus *Staphylococcus*, the genus *Bacillus*, the genus *Streptococcus*, the genus *Enterococcus*, or combinations thereof.

8. The method of claim 1, wherein the bacterial infection is the infection caused by at least one gram-negative microorganism selected from the group consisting of the genus *Salmonella*, the genus *Acinetobacter*, the genus *Escherichia*, the genus *Pseudomonas*, the genus *Klebsiella*, or combinations thereof.

9. The method of claim 1, wherein the bacterial infection is the infection caused by at least one gram-positive microorganism selected from the group consisting of *Staphylococcus aureus*, methicillin-resistant *Staphylococcus aureus* (MRSA), quinolone-resistant *Staphylococcus aureus* (QRSA), vancomycin resistant *Enterococcus* (VRE), vancomycin intermediate-resistant *S. aureus* (VISA), *Bacillus subtilis*, *Bacillus cereus*, *Streptococcus pneumoniae*, *Enterococcus faecalis*, *Staphylococcus epidermidis*, or combinations thereof.

10. The method of claim 1, wherein the bacterial infection is the infection caused by at least one gram-negative microorganism selected from the group consisting of *Salmonella typhimurium*, *Acinetobacter calcoaceticus*, *Acinetobacter baumanii*, *E. coli*, *Pseudomonas aeruginosa*, *Klebsiella aerogenes*, *Klebsiella pnemoniae*, or combinations thereof.

11. The method of claim 1, wherein the antibacterial composition is a pharmaceutical composition, a quasi-drug composition, a food composition, or a feed composition for livestock or fish.

12. The method of claim 1, wherein the condition is a disease selected from the group consisting of (i) to (iii) below:
   (i) pyogenic infection;
   (ii) food poisoning; and
   (iii) bacteremia, sepsis, urinary tract infection, pneumonia, pleural empyema, tympanitis, mastoiditis, meningitis, osteomyelitis, arthritis, peritonitis, pericarditis, cellulitis, typhus, and acute gastroenteritis.

13. A method of inhibiting a growth of a bacteria, comprising:
   applying, to a site suspected of the growth of the bacteria, a compound represented by Formula 1 or Formula 2, or a pharmaceutically acceptable salt thereof,

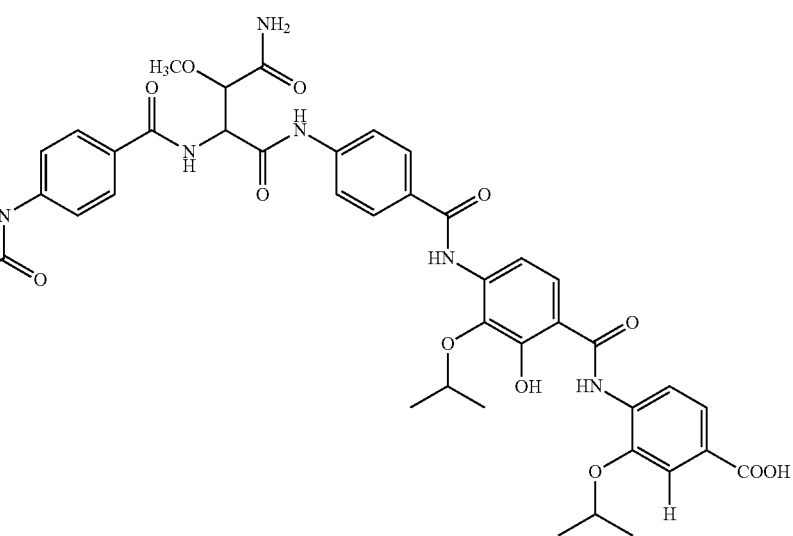

Formula 1

(Coralmycin A)

-continued

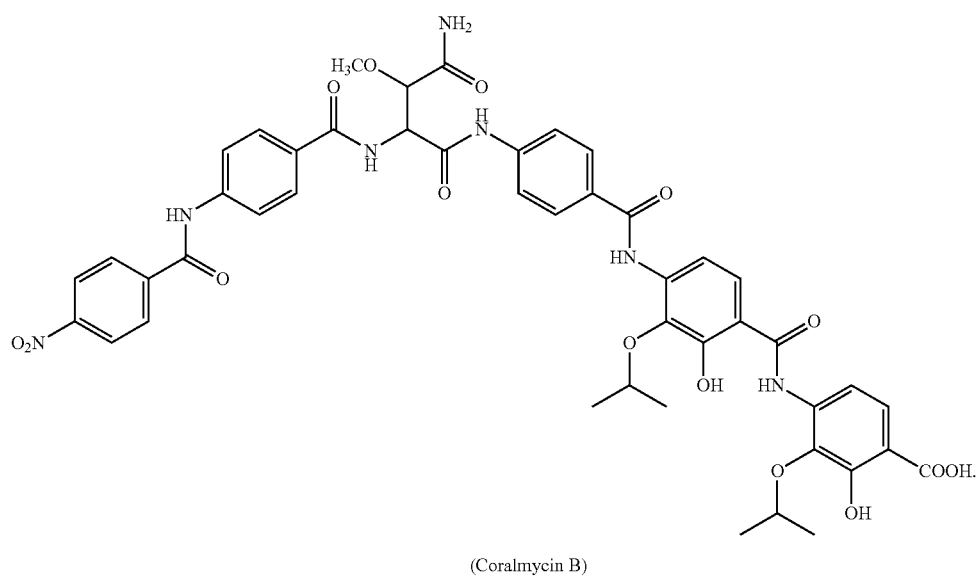

(Coralmycin B)

14. The method according to claim 13, wherein the bacteria is a gram-negative microorganism.

15. The method of claim 13, wherein the bacteria is a bacteria having antibiotics resistance.

16. The method of claim 15, wherein the antibiotics resistance is a resistance to at least one component selected from the group consisting of a penicillin antibiotic, a methicillin antibiotic, a quinolone antibiotic, a vancomycin antibiotic, a carbapenem antibiotic, and an aminoglycoside antibiotic.

17. The method of claim 13, wherein the bacteria is at least one gram-positive microorganism selected from the group consisting of the genus *Staphylococcus*, the genus *Bacillus*, the genus *Streptococcus*, the genus *Enterococcus*, or combinations thereof.

18. The method of claim 13, wherein the bacteria is at least one gram-negative microorganism of selected from the group consisting of the genus *Salmonella*, the genus *Acinetobacter*, the genus *Escherichia*, the genus *Pseudomonas*, the genus *Klebsiella*, or combinations thereof.

19. A method of treating a bacterial infection in a human, comprising administering an antibacterial composition to a subject in need thereof a compound represented by Formula 1 or Formula 2, or a pharmaceutically acceptable salt thereof:

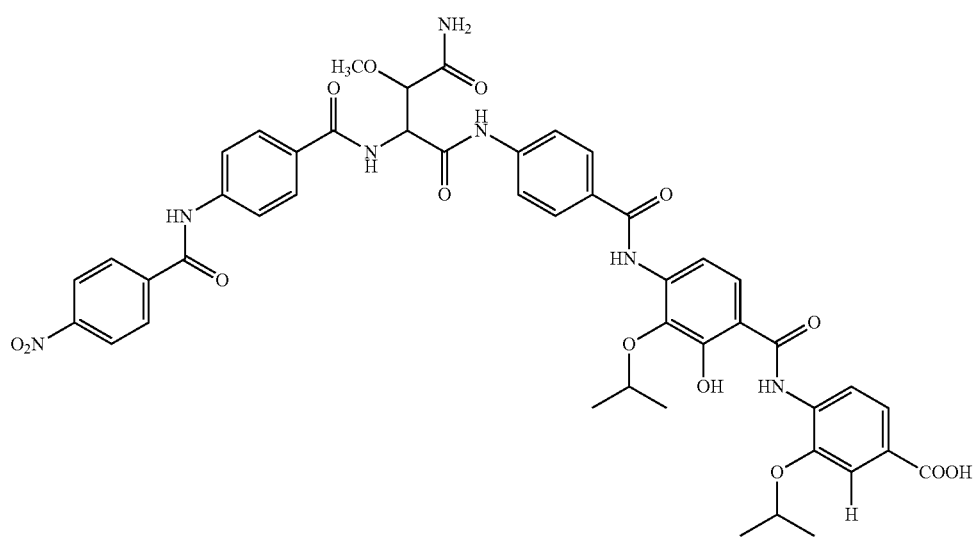

(Coralmycin A)

Formula 2
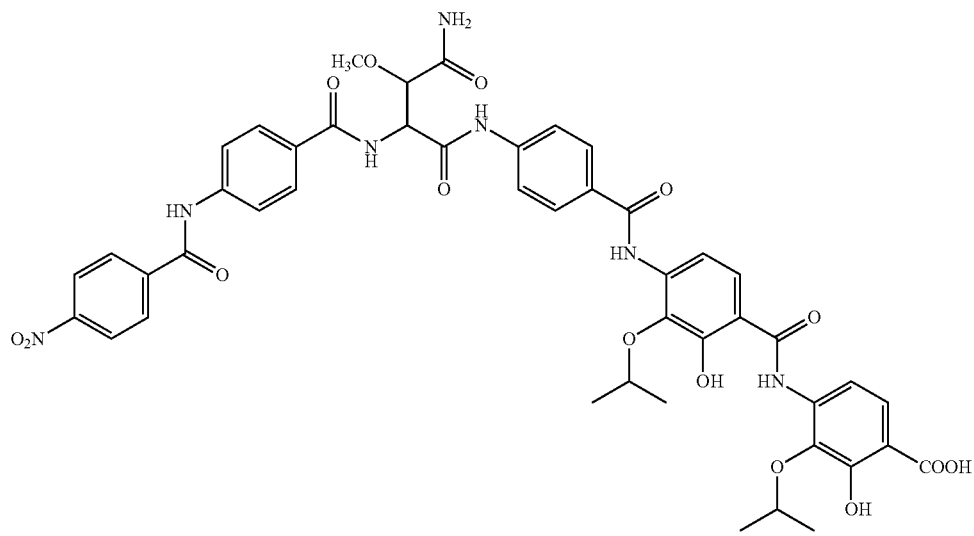
(Coralmycin B)
* * * * *